(12) United States Patent
Goodwin et al.

(10) Patent No.: US 8,795,147 B1
(45) Date of Patent: Aug. 5, 2014

(54) MODIFYING THE GENETIC REGULATION OF BONE AND CARTILAGE CELLS AND ASSOCIATED TISSUE BY EMF STIMULATION FIELDS AND USES THEREOF

(75) Inventors: Thomas J. Goodwin, Houston, TX (US); Linda C. Shackelford, Webster, TX (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 390 days.

(21) Appl. No.: 12/899,815

(22) Filed: Oct. 7, 2010

(51) Int. Cl.
*A61N 2/00* (2006.01)

(52) U.S. Cl.
USPC .................................. 600/9; 702/19

(58) Field of Classification Search
None
See application file for complete search history.

(56) References Cited

U.S. PATENT DOCUMENTS

| 4,839,046 | A |   | 6/1989  | Chandler |           |
|-----------|---|---|---------|----------|-----------|
| 4,988,623 | A |   | 1/1991  | Schwarz et al. | |
| 4,993,413 | A | * | 2/1991  | McLeod et al. | 607/2 |
| 5,002,890 | A |   | 3/1991  | Morrison | |
| 5,026,650 | A |   | 6/1991  | Schwarz et al. | |
| 5,153,132 | A |   | 10/1992 | Goodwin et al. | |
| 5,153,133 | A |   | 10/1992 | Schwarz et al. | |
| 5,155,034 | A |   | 10/1992 | Wolf et al. | |
| 5,155,035 | A |   | 10/1992 | Schwarz et al. | |
| 5,308,764 | A |   | 5/1994  | Goodwin et al. | |
| 5,627,021 | A |   | 5/1997  | Goodwin et al. | |
| 5,846,807 | A |   | 12/1998 | Goodwin | |
| 6,485,963 | B1 | * | 11/2002 | Wolf et al. | 435/298.2 |
| 6,673,597 | B2 |   | 1/2004  | Wolf et al. | |
| 6,730,498 | B1 |   | 5/2004  | Goodwin et al. | |
| 6,919,205 | B2 |   | 7/2005  | Brighton | |
| 7,160,241 | B1 |   | 1/2007  | Herbst | |
| 7,179,217 | B2 |   | 2/2007  | Goodwin et al. | |
| 7,456,019 | B2 |   | 11/2008 | Goodwin et al. | |
| 2006/0229487 | A1 | * | 10/2006 | Goodwin et al. | 600/13 |
| 2007/0105769 | A1 | * | 5/2007  | Simon | 514/12 |
| 2008/0138415 | A1 | * | 6/2008  | Hussain et al. | 424/486 |
| 2009/0234417 | A1 | * | 9/2009  | Pastena et al. | 607/40 |
| 2011/0105959 | A1 | * | 5/2011  | O'Connor | 601/2 |

OTHER PUBLICATIONS

Au et al in "Interactive effects of surface topography and pulsatile electrical field stimulation on orientation and elongation of fibroblasts and cardiomyocytes" (Biomaterials: 2007, vol. 28, No. 29, pp. 4277-4293).*
Hammond et al in "Optimized suspension culture: the rotating-wall vessel" (Am J Physiol Renal Physiol, 2001: vol. 281, pp. F12-F25).*
Reddy et al in "Micronuclei in Blood and Bone Marrow Cells of Mice Exposed to Specific Complex Time-Varying Pulsed Magnetic Fields" (Bioelectromagnetics: 2010, vol. 31, pp. 445-453; published online Apr. 10, 2010).*

* cited by examiner

*Primary Examiner* — Catherine Hibbert
(74) *Attorney, Agent, or Firm* — Theodore U. Ro

(57) ABSTRACT

An apparatus and method to modify the genetic regulation of mammalian tissue, bone, or any combination. The method may be comprised of the steps of tuning at least one predetermined profile associated with at least one time-varying stimulation field thereby resulting in at least one tuned time-varying stimulation field comprised of at least one tuned predetermined profile, wherein said at least one tuned predetermined profile is comprised of a plurality of tuned predetermined figures of merit and is controllable through at least one of said plurality of tuned predetermined figures of merit, wherein said plurality of predetermined tuned figures of merit is comprised of a tuned B-Field magnitude, tuned rising slew rate, tuned rise time, tuned falling slew rate, tuned fall time, tuned frequency, tuned wavelength, and tuned duty cycle; and exposing mammalian chondrocytes, osteoblasts, osteocytes, osteoclasts, nucleus pulposus, associated tissue, or any combination to said at least one tuned time-varying stimulation field comprised of said at least one tuned predetermined profile for a predetermined tuned exposure time or plurality of tuned exposure time sequences.

20 Claims, 7 Drawing Sheets

MODIFYING THE GENETIC REGULATION OF BONE AND CARTILAGE CELLS AND ASSOCIATED TISSUE BY EMF STIMULATION FIELDS AND USES THEREOF

ORIGIN OF THE INVENTION

The invention described herein was made by employees of the United States Government and may be manufactured and used by or for the Government of the United States of America for governmental purposes without the payment of any royalties thereon or therefor.

BACKGROUND OF THE INVENTION

1. Field of the Innovation

The present innovation relates generally to the fields of biophysics, bioelectromechanics, tissue regeneration, tissue culture, and neurophysiology. More specifically, the present innovation relates to the use of an electromagnetic field, and preferably, a time-varying magnetic field, for modifying, potentiating or controlling the growth and specific genetic expression of biological cells and tissue, such as mammalian tissue. More specifically, the present innovation relates to the use of a noninvasive method and apparatus comprising relatively low frequency magnetic fields for modifying the genetic regulation of mammalian chondrocytes, osteoblasts, osteocytes, osteoclasts, nucleus pulposus, associated tissue, or any combination.

2. Background and Related Art

Cartilage

Cartilage is a type of dense connective tissue existing within many joints. It is composed of specialized cells called chondrocytes that produce a large amount of extracellular or cartilaginous matrix comprised of actin and collagen fibers, proteoglycans, glycosaminoglycans, and elastin fibers. Chondrocytes are the only cells found in cartilage. Cartilage is classified in three types, elastic cartilage, hyaline cartilage, and fibrocartilage. Cartilage is found in many areas in a mammalian body, including the articular surface of the bones, the rib cage, the ear, the nose, the bronchial tubes and the intervertebral discs. Its mechanical properties are intermediate between bone and dense connective tissue like tendon. (Cartilage, 2010)

Unlike other connective tissues, cartilage does not contain blood vessels or is referred to as avascular. The chondrocytes are fed by diffusion, helped by the pumping action generated by compression of the articular cartilage or flexion of the elastic cartilage. Thus, compared to other connective tissues, cartilage grows and repairs more slowly. (Cartilage, 2010)

There are several diseases which can affect the cartilage. Chondrodystrophies are a group of diseases characterized by disturbance of growth and subsequent ossification of cartilage. Osteoarthritis (OA) is a common disease affecting cartilage. Osteoarthritis, also known as a degenerative joint disease, is a group of mechanical abnormalities involving degradation of joints, including articular cartilage and subchondral bone. The cartilage covering bones (articular cartilage) is thinned, eventually completely worn out, resulting in a "bone against bone" joint, reduced motion, and pain. Osteoarthritis is very common, affects the joints exposed to high stress, and is therefore considered the result of "wear and tear" rather than a true disease. The usual symptoms are stiffness, limitation of motion, and pain. Osteoarthritis is the most common form of arthritis, and prevalence rates increase markedly with age. It has been shown that elderly patients with self-reported osteoarthritis visit doctors twice as frequently as their unaffected peers. Such patients also experience more days of restricted activity and bed confinement compared to others in their age group. (Cartilage, 2010)

Cartilage has limited repair capabilities, because chondrocytes are bound in lacunae, they cannot migrate to damaged areas. Therefore, if damaged, cartilage is difficult to heal. Also, because hyaline cartilage does not have a blood supply, the deposition of new cartilaginous matrix is slow. Damaged hyaline cartilage is usually replaced by fibrocartilage scar tissue. (Cartilage, 2010)

Acetaminophen/paracetamol is generally used as a first line treatment and anti-inflammatory drugs (NSAIDs) are only recommended as add on therapy if pain relief is not sufficient. This is due to greater safety of acetaminophen as opposed to NSAIDS. In addition, to these treatments, several cartilage regeneration techniques have been developed. These techniques include the following: (1) debridement or abrasion—surgeon arthroscopically removes loose cartilage which causes bleeding at the bone surface and growth of fibrocartilage (fibrous cartilage or scar tissue) but the fibrocartilage may not be strong enough; (2) microfracture—surgeon arthroscopically clears the affected area and makes several perforations in the bone to stimulate bleeding and growth of fibrocartilage; (3) mosaicpiasty or osteochondral autograft transplantation surgery—surgeon removes a plug of bone with cartilage covering from a healthy area of the joint and transplants it to the damaged area; (4) periosteal flap—surgeon removes a portion of the periosteum (connective tissue covering all bones) from shin and transplants it to the area of cartilage damage; (5) autologous chondrocyte implantation—surgeon arthroscopically removes small portion of cartilage from knee; tissue is sent to a lab to be cultured; second surgery required so lab-grown cells can be implanted at the site of the damaged cartilage; and (6) osteochondral allografts—donor bone is used to repair the damaged cartilage. These procedures yield mixed and often inconsistent results. There are still many questions that plague attempts at cartilage regeneration. There is a need to find definitive answers and to develop procedures that relieve arthritis symptoms and produce a durable replacement for damaged cartilage.

Bone

Bones are rigid organs that form part of the endoskeleton of vertebrates. Bones function to move, support, and protect the various organs of the body, produce red and white blood cells and store minerals. Bone tissue is a type of dense connective tissue. Bones comprise an organic component of cells and matrix as well as an inorganic or mineral component. Because bones come in a variety of shapes and have a complex internal and external structure they are lightweight, yet strong and hard, in addition to fulfilling their many other functions. One of the types of tissue that makes up bone is the mineralized osseous tissue, also called bone tissue, which gives it rigidity and a honeycomb-like three-dimensional internal structure. Other types of tissue found in bones include marrow, endosteum and periosteum, nerves, blood vessels and cartilage. (Bone, 2010)

There are several types of cells constituting the bone. For example, osteoblasts are mononucleate bone-forming cells that descend from osteoprogenitor cells. They are located on the surface of osteoid seams and make a protein mixture known as osteoid, which mineralizes to become bone. Osteoid is primarily composed of Type I collagen. Osteoblasts also manufacture hormones, such as prostaglandins, to act on the bone itself. They robustly produce alkaline phosphatase, an enzyme that has a role in the mineralization of bone, as well as many matrix proteins. Osteoblasts are the immature bone cells. In addition, bone lining cells are essentially inactive osteoblasts. They cover all of the available bone surface and function as a barrier for certain ions. Still further, osteocytes originate from osteoblasts that have migrated into and become trapped and surrounded by bone matrix that they themselves produce. The spaces they occupy are known as lacunae. Osteocytes have many processes that reach out to meet osteoblasts and other osteocytes probably for the purposes of communication. Their functions include to varying degrees: formation of bone, matrix maintenance and calcium homeostasis. They have also been shown to act as mechanosensory receptors—regulating the bone's response to stress and mechanical load. They are mature bone cells. Finally, osteoclasts, a form of macrophage, are the cells responsible for bone resorption (remodeling of bone to reduce its volume). Osteoclasts are large, multinucleated cells located on bone surfaces in what are called Howship's lacunae or resorption pits. These lacunae, or resorption pits, are left behind after the breakdown of the bone surface. Because the osteoclasts are derived from a monocyte stem-cell lineage, they are equipped with phagocytic like mechanisms similar to circulating macrophages. Osteoclasts mature, migrate, or both to discrete bone surfaces. Upon arrival, active enzymes, such as tartrate resistant acid phosphatase, are secreted against the mineral substrate. (Bone, 2010)

In the disease commonly known as osteoporosis, bone demineralizes and becomes abnormally rarefied. The cells and matrix of a bone comprise a framework of collagenous fibers which is impregnated with the mineral component of calcium phosphate (~85%) and calcium carbonate (~10%) which imparts rigidity to the bone. While osteoporosis is generally thought of as afflicting the elderly, certain types of osteoporosis may affect persons of all ages whose bones are not subject to functional stress. In such cases, patients may experience a significant loss of cortical and cancellous or trabecular bone during prolonged periods of immobilization. Elderly patients are known to experience bone loss due to disuse when immobilized after fracture of a bone, which may ultimately lead to a secondary fracture in an already osteoporotic skeleton. Diminished bone density may lead to vertebrae collapse, fractures of hips, lower arms, wrists, ankles as well as incapacitating pains.

Current therapies comprise invasive procedures (e.g. surgery or drug administration) as opposed to the described innovation which is a non-invasive procedure. Alternative nonsurgical therapies for such diseases include electrical bone growth stimulation comprised of electric and magnetic field therapies. However these therapies are moderately invasive as they rely on either skin contact or insertion of probes/electrodes into the tissue to achieve the desired results.

Nucleus Pulposus

Nucleus pulposus is the jelly-like substance in the middle of the spinal disc. It functions to distribute hydraulic pressure in all directions within each disc under compressive loads. The nucleus pulposus comprises disc chondrocytes (as opposed to articular chondrocytes), collagen fibrils, and proteoglycan aggrecans that have hyaluronic long chains which attract water. Attached to each hyaluronic chain are side chains of chondroitin sulfate and keratan sulfate. (Nucleus pulposus, 2008)

Electric and Magnetic Fields

An electric field is a property that describes the space that surrounds electrically charged particles. Electric fields are created by differences in electric potential or voltage: i.e., the higher the voltage, the stronger will be the resultant electric field. In contrast, magnetic fields that are generated electromagnetically are created when electric current flows: i.e., the greater the current, the stronger the magnetic field. An electric field will exist even when there is no current flowing. In contrast, a magnetic field generated electromagnetically will not exist when there is no current. If current does flow, the strength of the magnetic field that is generated electromagnetically will vary with power consumption but the electric field strength will be constant. Resultant forces are related to both electric and magnetic fields. The force associated with an electric field depends on a stationary or static charge. Conversely, the force exerted on a charged particle associated with a magnetic field (i.e., Lorentz force) depends on a moving charge. Further, electric and magnetic fields are not entirely mutually exclusive. For example, charged particles do not only produce electric fields. As charges move, they generate magnetic fields, and if the magnetic field changes, the change in said magnetic field will generate electric fields. Thus weak metals (ions) such as CA2+, K+, Li+, and Mg2+ are all subject to modulation or resonance effect and can be made to move sub-cellularly due to magnetic flux. Stated differently, a changing magnetic field gives rise to an electric field. In nature lightning is an example of an atmospheric electrical discharge that creates an attendant magnetic field.

Electrical Stimulation Therapies

Electrical stimulation therapies include: capacitive coupling (CC); and direct current (DC) or direct coupling. The original basis for forms of electric stimulation therapy was the observation that physical stress on bone causes the appearance of tiny electric currents (i.e., a piezo-electric effect) that, along with mechanical strain, were thought to be the mechanisms underlying transduction of the physical stresses (compression and tension) into an electrical signal that promotes bone formation. CC relies on an electric field that is generally generated by 2 capacitive plates or electrodes placed on a patient's skin on opposite ends of a region of interest to apply electrical stimulation in the region of interest. DC-based therapies require the placement of opposing electrodes in direct contact with the skin surface surrounding the tissue of interest (Trock, 2000) and generally involve implantation of the electrodes. The region of interest is stimulated by a constant direct current.

Magnetic Field Therapies

Magnetic field therapies include: time-varying magnetic field (TVMF) therapies including pulsed electromagnetic field (PEMF) therapies. The general use of time-varying magnetic fields to stimulate the growth of cells has been previously disclosed in the related art. It has been theorized that the piezo-electric properties in human tissue such as bone and cartilage forms the basis for regulating bone and cartilage formation. Specifically, because a magnetic field imposes a force on magnetic particles and moving electrically charged particles, the magnetic field forces simulate physical stress in human tissue thereby resulting in small, induced currents (Faraday currents) in the tissue's highly conductive extracellular fluid. In general, time-varying magnetic field therapies involve the use of coils to electrically generate a magnetic field. PEMFs are considered a subset of time-varying magnetic field therapies and are generally associated with pulses or bursts in its waveforms. Resultant waveforms used in PEMF therapies can be substantially monophasic, substantially biphasic, substantially square, sinusoidal, or substantially triangular. Further, PEMF therapies are generally comprised of frequencies on the lower end of the electromagnetic spectrum such as from 6-500 Hz. Further, waveforms used in PEMF therapies generally have high rising and falling slew rates on the order of Tesla/sec, thereby promoting said pulses or bursts.

In U.S. Pat. No. 7,179,217 an apparatus for enhancing tissue repair in mammals is disclosed. The disclosed apparatus comprises: a sleeve for encircling a portion of a mammalian body part, said sleeve comprising an electrically conductive coil capable of generating a magnetic field when an electrical current is applied thereto, means for supporting the sleeve on the mammalian body part; and a means for supplying the electrically conductive coil with a square wave time-varying electrical current sufficient to create a time-varying magnetic force of from approximately 0.05 G to 0.5 G within the interior of the coil in order that when the sleeve is placed on a mammalian body part and the time-varying magnetic force of from approximately 0.05 G to 0.5 G is generated on the mammalian body part for an extended period of time, tissue regeneration within the mammalian body part is increased to a rate in excess of the normal tissue regeneration rate that would occur without application of the time-varying magnetic force. The electrically conductive coil is preferably a ferromagnetic material, such as wire, with approximately ten windings per inch. The sleeve can be placed on a body part, e.g. an arm or a leg, of the mammal and the body part exposed to the 0.05 G to 0.5 G time-varying magnetic force for an extended period of time to enhance tissue repair, such increasing the healing rate of bone fracture repair or increased healing rate of ulcerated skin. It is preferable that the treated mammal is provided an increased level of calcium ions (Ca+ or Ca++) during the application of the time-varying magnetic force.

Anabolic and Catabolic Gene Expressions

Scientists have traditionally classified hormones into two categories: anabolic or catabolic, depending on which part of metabolism they stimulate. The traditional anabolic hormones are the anabolic steroids, which stimulate protein synthesis and muscle growth. Conversely, the traditional catabolic hormones are adrenaline (and other catecholamines). In recent decades, many more hormones with at least some effects have been discovered, including cytokines or paracrine and autocrine factors which are the products of genomic up or down regulations. The combination of anabolic and catabolic effects is by no means the sum and total of the genomic capacity to stimulate reconstructive changes within the physiology. Further specific genes and some molecules work in concert with each other or in gene cascades (chaperones) which facilitate the end goal of tissue remodeling, with processes such as glucose metabolism fluctuating to match an animal's normal periods of activity throughout the day (Ramsey, Marcheva, Kohsaka, & Bass, 2007).

Similarly, known biomolecules such as vitamins are extremely useful in perpetuating the process of normal cartilage and bone maintenance. Two such molecules are Vitamin (specifically D3) and Vitamin K. The actions of these vitamins are known to a degree in relation to normal mammalian (specifically human) physiology (Ishikawa, 2006), (Atkins, 2009), (Koshihara, 1997). The inventors postulate that due to the facilitated stimulation of important gene expressions (specifically osteocalcin up-regulation which was unanticipated as part of the responding cascade) that addition of increased concentrations of these two vitamins during treatment of the affected area (ROI) in any outlined regime or matrix will further enhance and accelerate the formation of new bone and differentiate the expression of bone from cartilage in the subject tissue as mineralization will produce bone and not cartilage. Osteocalcin is known to be a biological cofactor which when exposed to increased amounts of Vitamin K leads to mineralization of new bone. Thus, addition of Vitamin D3 in concentrations from 200-1000 IU daily and Vitamin K from about 50 to about 2000 mg daily will further facilitate the regeneration (anabolic effects) of bone and differentiate bone from cartilage formation. Additionally, osteocalcin is also tied to energy generation (needed especially for rapid cell growth) by modulating the production of insulin.

Anabolism is the set of metabolic pathways or genomic and protein responses that construct molecules from smaller units (de Bolster, 1997). These reactions require an energy system which in the case of cells is derived from other genomic responses in the breakdown of energy "packets" in the cell. One way of categorizing metabolic processes, whether at the cellular, organ or organism level is as anabolic or as catabolic, which is the opposite of anabolic. Anabolism is powered by catabolism, where large molecules are broken down into smaller parts and then used up in oxidative metabolism of respiration. Many if not all anabolic processes are powered by adenosine triphosphate (ATP), adenosine diphosphate (ADP) or adenosine monophosphate (AMP) (Nicholls & Ferguson, 2002). Anabolic processes are generally associated with "building up" or regeneration of organs and tissues. These processes produce growth and differentiation of cells and increase in organ or body size, a process that involves manufacture and production of complex building blocks known as molecules. Classic examples of anabolic processes include the regeneration, growth of cartilage, growth and mineralization of bone and increases in muscle mass and complexity. In genomic terms and for the purposes herein, "anabolic" will be associated with the building of tissue or the regeneration of tissue from an organic perspective.

Catabolism is the set of pathways that break down molecules into smaller units and release energy (de Bolster, 1997). In catabolism, large molecules such as nucleic acids, proteins, polysaccharides, and lipids, and are broken down into smaller units such as amino acids, nucleotides, monosaccharides, and fatty acids, respectively. As molecules such as polysaccharides, proteins, and nucleic acids are made from long chains of these small monomer units, the large molecules are called polymers. Cells use the monomers released from breaking down polymers to either construct new polymer molecules, or degrade the monomers further to simple waste products, releasing energy. Cellular wastes include lactic acid, acetic acid, carbon dioxide, ammonia, and urea which require scavenger molecules to "clean up" so as not to pollute the organic system. Creation of these wastes is a function of the oxidation process involving a release of chemical energy, some of which is lost as heat, but the rest of which is used to drive the synthesis of adenosine triphosphate (ATP). This molecule acts as a way for the cell and thus the organism to transfer the energy released by catabolism to the energy-requiring reactions (genomic functions) that make up anabolism or construction of the tissue. These anabolic processes are controlled by genomic cascades which "cooperate" to achieve the desired end result; that of formation of new tissue. This catabolism provides the chemical energy and genomic instruction necessary for the maintenance and growth of cells, which can be referred to as a reparative function. In genomic terms, catabolism is the reorganization or destruction of tissue such as one sees in osteoarthritis or osteoporosis. Thus the process of bone remodeling and osteoclastogenesis are examples of a catabolic event driven by genes specifically associated with the process. For the purposes of herein, "catabolic" will be associated with a reparative function and specifically, the breakdown, reorganization, or the degeneration of tissue from an organic perspective.

Currently, full advantage is not being taken of the use of these biophysical and electrical stimuli in the health care professions, due to lack of knowledge and education in this field. However, as the underlying mechanisms at the molecular and cellular level become understood, it is hoped that these stimuli will be better defined and utilized, and as a result, medical instrumentation using this medical technology will therefore become more widely implemented in the clinical and out-patient setting. Currently, the related art primarily depends on frequency and B-Field magnitude associated with an electromagnetic field waveform for the stimulated growth of biological cells and associated tissue. In fact, related art publications indicate that a B-Field magnitude is the primary control variable for affecting biological cell and tissue growth. At some point, the B-field magnitude's effect becomes more of a thermal effect as compared to a physical force imparted at the cellular level. For example any magnetic field greater than 30 kHz falls into the radio frequency range and is known to result in thermal heating effects at the sub-cellular level. The related art is deficient in discovery of a specific stimulation field profile necessary for up-regulating and down-regulating specific genes, wherein said profile is comprised of not only frequency and B-Field magnitude, but also waveform shape, rise time, rising slew rate, fall time, falling slew rate, duty cycle, dwell time, time of exposure, and other possible factors. The therapeutic implications of the discovery of specific profiles associated with stimulating specific genes will be explained herein. Thus, it would be desirable to provide an apparatus and method of use which would promote the stimulation of specific genes by a specific stimulation field of predetermined profile.

SUMMARY OF THE INVENTION

The present invention relates to a system and method to modifying the genetic regulation of mammalian chondrocytes, osteoblasts, osteocytes, osteoclasts, nucleus pulposus, associated tissue, or any combination. There are multiple embodiments with respect to what comprises "associated tissue". For example, associated tissue may comprise cartilaginous tissue, osseous tissue, connective tissue, cancellous tissue, tendon and muscle, or any combination, etc. More specifically, the act of modifying may be comprised of promoting the retention, repair of and reduction of compromised cartilage, bone, and associated tissue in a mammalian system by preferential stimulation of the aforementioned cell types in the mammalian physiology in a specific order or sequence. A stimulation field generator may be used to deliver a tuned time-varying stimulation field profile of predetermined performance characteristics or Figures of Merit (FOM) to the targeted tissue for a predetermined tuned exposure time or plurality of tuned exposure time sequences wherein said FOMs may comprise B-Field magnitude, frequency, wavelength, rising slew rate, falling slew rate, rise time, fall time, and duty cycle(s). The apparatus may include several components comprising: 1) a power source, 2) control component, and 3) a transmission component. The power source supplies the electricity necessary to produce an electromagnetically generated time-varying stimulation field of predetermined profile that is controlled and governed by the control component of the apparatus wherein said time-varying stimulation field is induced to a target tissue or region of interest (ROI) by a transmission component. The transmission component may take the embodiment of standard transmission antennae, magnetic coils, a complexed array that consists of multiple coils, antennae to deliver the correct magnetic field to the ROI in the proper field density, or any combination. In an embodiment, the apparatus delivers a tuned time-varying stimulation field comprising at least one tuned predetermined profile to preferentially stimulate (up-regulate, down-regulate, or a combination of both) the biochemical cellular and sub-cellular molecular responses to trigger the activation of known mammalian genes responsible for the regeneration, restoration, repair, maintenance, or any combination of cartilage, bone, or both.

Accordingly, it is an object of the present innovation to provide an apparatus for biomedical therapeutic applications based on the application of time-varying magnetic fields, and more particularly to TVMFs produced in a device which utilizes a tuned electrical signal capable producing a tuned predetermined time-varying stimulation field comprised of at least one tuned predetermined profile at a treatment site for cartilage, bone, and soft tissue therapy.

It is another object of the present innovation to provide a multi-functional, modular device using wire coils that create a tuned predetermined time-varying stimulation field of at least one tuned predetermined profile designed for penetration into cartilage, bone, associated tissue, or any combination for the treatment of osteoarthritis, fractures, osteoporosis, and the like.

It is a further object of the invention to provide at least one tuned electrical signal based on frequency, amplitude, rise time, rising slew rate, fall time, falling slew rate, duty cycle, dwell cycle(s), or any combination to a stimulation field generator apparatus in order to generate and emit a tuned time-varying stimulation field of at least one tuned predetermined profile that will result in modifying the genetic regulation of the aforementioned mammalian cells.

It is yet another object of the invention to provide time-varying magnetic field neuromuscular stimulation utilizing a predetermined time-varying stimulation field for reducing muscle atrophy as a countermeasure to body unloading effects.

In an embodiment, the apparatus may emit and deliver to the target area or tissue a substantially square wave between about 9 Hz to about 200 Hz; with a rise time between about 125 μs to about 1 ms; a rising slew rate of between about 2.0 kG/s to about 50.0 kG/s; a fall time between about 125 μs to 1 ms; a falling slew rate of between about 2.0 kG/s to about 500.0 kG/s, or any combination. Additionally, the apparatus may operate on a duty cycle of between about 65% to about 80% (and a subsequent dwell time of between about 35% to about 20%, respectively). Still further, the apparatus may operate for a predetermined tuned exposure time from about 1 hour to about 1200 hours in a continuous manner or based on a predetermined time schedule. Deviations from these FOMs may elicit deferential responses with regard to mammalian cells, ion transport, and thus genetic and protein expression.

In an embodiment, the innovation is a method comprising the steps of positioning an apparatus in a predetermined proximate spatial relationship to a region of interest comprising damaged chondrocytes, osteoblasts, osteocytes, osteoclasts, nucleus pulposus, or any combination, wherein said apparatus is capable of producing a time-varying stimulation field; generating a predetermined time-varying stimulation field in the form of a substantially square waveform with a B-Field magnitude from about 0.6 G to about 50 G, a frequency from about 9 Hz to about 200 Hz, a rise time of from about 0.75 ms to about 1 ms, rising slew rate from about 2.0 kG/s to about 20.0 kG/s, a fall time from about 125 μs to about 300 μs, a falling slew rate from about 5.0 kG/s to about 50.0 kG/s, and a duty cycle from about 65% to about 80%, and wherein said stimulation field promotes the growth of chondrocytes, osteoblasts, osteocytes, osteoclasts, nucleus pulposus, or any combination.

In an embodiment, the innovation is a method comprising the steps of providing an apparatus comprising a power source, control component, and a transmission component; positioning a region of interest comprising damaged chondrocytes, osteoblasts, osteocytes, osteoclasts, nucleus pulposus, or any combination in proximate spatial relationship to said apparatus; operating said apparatus to generate time-varying stimulation filed comprised of a substantially square wave with a frequency from about 9 Hz to about 200 Hz, a rise time of from about 0.75 ms to about 1 ms, rising slew rate from about 2.0 kG/s to about 20.0 kG/s, a fall time from about 125 µs to about 300 µs, and a falling slew rate from about 5.0 kG/s to about 50.0 kG/s, wherein the duty cycle of said square wave is from about 65% to about 80%, wherein the operation of said apparatus produces said time-varying stimulation field, and wherein the stimulation field promotes the growth of chondrocytes, osteoblasts, osteocytes, osteoclasts, nucleus pulposus, or any combination. With particular reference to FIG. 6, in another embodiment, power source, control component, transmission component, or any combination is incorporated in a sleeve 20 (such as for example, described in U.S. Pat. No. 7,179,217 (Goodwin & Parker, 2007)), wherein the power source, control component, and transmission component are operably connected to each other. The sleeve is capable of wrapping around a ROI 21, such as a body part or an appendage of a mammalian physiology and is capable of delivering a magnetic field 34 to said ROI.

In an embodiment, a pulsed stimulation field of predetermined profile may be used in combination with (either serially or in parallel) a time-varying stimulation field of predetermined profile for determining differential matrix signaling for accomplishing various therapeutic applications. In another embodiment, the control component controls predetermined characteristics of one or more fields. In still another embodiment, the control component is comprised of a conductor, an amplifier, or both.

In an embodiment, the stimulation field is comprised of a magnetic field of a predetermined profile capable of accomplishing CA2+ ionic transport modulation for mammalian chondrocytes, osteoblasts, osteocytes, osteoclasts, nucleus pulposus, associated tissues, or any combination. In another embodiment, the stimulation field is comprised of a magnetic field of a predetermined profile capable of modifying the genetic regulation of mammalian chondrocytes, osteoblasts, osteocytes, osteoclasts, nucleus pulposus, associated tissue, or any combination. In still another embodiment, the stimulation field is capable of producing or suppressing specific biomolecules that are associated with and necessary and responsible for the growth, retention, regeneration and repair of chondrocytes, osteoblasts, osteoclasts, osteocytes, and nucleus pulposus.

In an embodiment, the predetermined time-varying simulation field is capable of modifying the genetic regulation of mammalian chondrocytes, osteoblasts, osteocytes, osteoclasts, nucleus pulposus, associated tissues, or any combination to increase the growth rate of these cells and tissues greater than the normal physiological rates of growth. In another embodiment, the predetermined time-varying stimulation field is capable of being regulated to enhance the growth, retention, restoration, and repair of cells associated with activating gene families including, but not limited to: BMP, Actin, Thrombospondins, Lamanins, Proteoglycans, Collagens, Tumor Necrosis Factors (TNF), Transforming Growth Factors TGF, and Cytoskeletal families.

As used in this paper, a "stimulation field" refers to a magnetic field generated electromagnetically wherein the magnetic field is comprised of a B-Field wherein a particle having an electric charge, q, and moving in said B-field with a velocity, v, experiences a physical force. Further, as used in this paper, a "region of interest" is defined as an area targeted to be exposed to a stimulation field. A region of interest can be, for example; a rotating wall vessel containing biological materials or a predetermined area on a patient's body. Still further, as used in paper, a "profile" refers to a waveform. In addition, "figures of merit" refer to measurable performance characteristics or values. Still further, "anabolic" refers to the building of tissue or the regeneration of tissue from an organic perspective. "Catabolic" refers to a reparative function and specifically, the breakdown, reorganization, or the degeneration of tissue from an organic perspective. HCH as used herein refers to human chondrocytes. HOB as used herein refers to human osteoblasts. As used herein, NOR refers to no or zero differential regulation. As used herein, NRF refers to no regulated effect. As used herein in the claim(s), when used in conjunction with the word "comprising", the words "a" or "an" mean one or more.

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION

Figure 1:
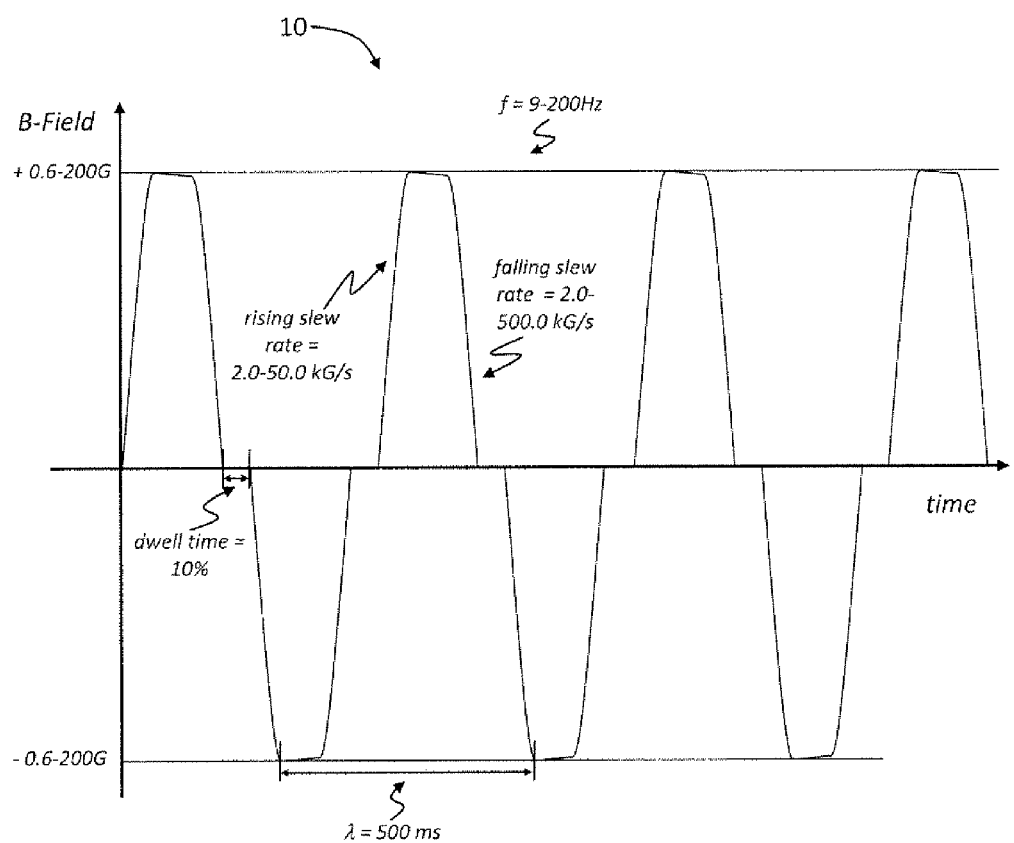
FIG. 1 depicts an exemplary stimulation field profile of a substantially biphasic, square waveform.

The innovation utilizes stimulation fields of at least one predetermined profile to modify the genetic regulation of mammalian chondrocytes, osteoblasts, osteocytes, osteoclasts, nucleus pulposus, associated tissues, or any combination. In an embodiment, the at least one predetermined profile is tuned in accordance with empirical techniques. Various embodiments of the apparatus and method are applicable but are not limited to the diseases of osteoarthritis and osteoporosis as well as to be used to treat and resolve damaged structures of the skeletal and soft or connective tissues of the physiology. The innovation described herein uses a completely non-invasive method and protocol to affect the desired results outlined above. The innovation also relates to a method of treating diseased tissue in a human through the exposure of a tuned or tunable stimulation field of at least one tuned predetermined profile to diseased tissue in a human, including osteoarthritis, osteoporosis, osteopenia, and other cartilage/bone diseases, defects, and injuries.

In an embodiment, the method includes steps associated with tuning or selecting a tuned predetermined time-varying stimulation field of at least one tuned predetermined profile for at least one predetermined time period wherein different profiles may be employed for different periods of time. It is well known that an electrical current flowing through a wire generates a magnetic field. The resultant magnetic field is produced by the motion of electrical charges, i.e., electrical current. However, the specific manner of tuning electrical signal characteristics or FOMs and to produce a tuned predetermined time-varying stimulation field to optimize the re-growth of tissue based on cellular and sub-cellular observations is not well-known in the related art. The innovation described herein attempts to solve at least some of the problems described above.

In an embodiment, the innovation is comprised of a device that can be wrapped around a ROI such as, for example, joints where damaged cartilage is located. The device may produce at least one stimulation field at a pre-determined frequency, wavelength, magnitude, rise time, rising slew rate, fall time, falling slew rate, duty cycle, or any combination that will result in tissue modification. For example, this embodiment addresses problems associated with invasive surgical techniques by non-invasively applying a TVMF to the affected areas to regenerate and re-grow cartilage cells, bone cells, or both.

As an example in an embodiment, the inventors have determined that successful reproducible transmission of electrically generated stimulation fields of predetermined frequency are comprised of five factors: (1) the profile or waveform of the stimulation field comprising predetermined FOMs; (2) a sufficient field flux to overcome the ambient environment; (3) design of a transmission component (antennae); (4) change of slew rate and rise and fall time; and (5) exposure time of the ROI to the stimulation field. The innovation described herein is associated with the inventors' laboratory studies at the cellular level designed to elucidate the fundamental underlying mechanisms that link stimulation field exposure to biological effects. Specifically, the results of the inventors' research identify mechanisms based on molecular or cellular changes that are brought about by stimulation fields of predetermined profile thereby providing clues as to how a physical force is converted or transduced into a biological action within a mammalian physiology.

Figure 7:
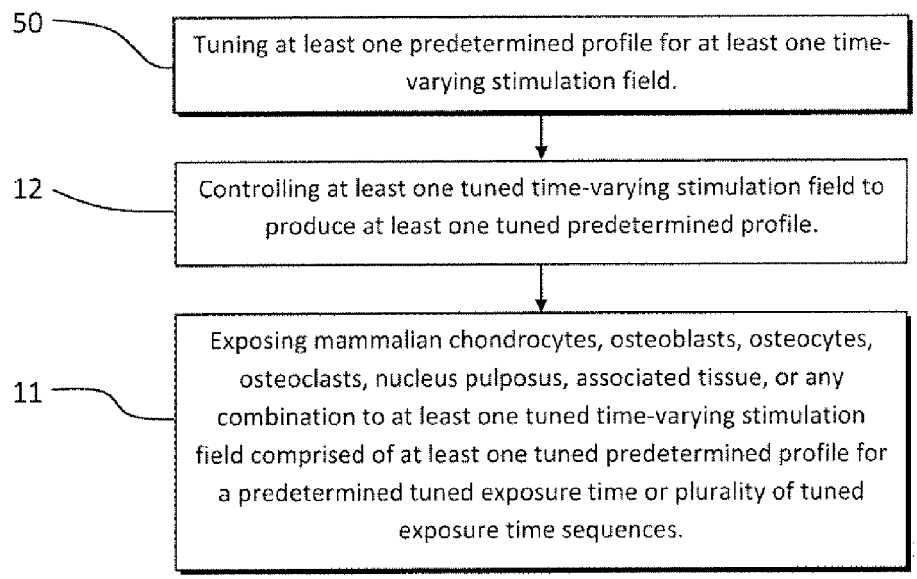
FIG. 7 depicts a flowchart of a method to modify the genetic regulation of mammalian tissue, bone, or any combination comprising the steps of: exposing said mammalian chondrocytes, osteoblasts, osteocytes, osteoclasts, nucleus pulposus, associated tissue, or any combination to at least one tuned time-varying stimulation field.

With particular reference to FIG. 7, for example, in an embodiment, the innovation comprises a method to modify the genetic regulation of mammalian tissue, bone, or any combination comprising the steps of: exposing said mammalian chondrocytes, osteoblasts, osteocytes, osteoclasts, nucleus pulposus, associated tissue, or any combination to at least one tuned time-varying stimulation field 11 comprised of at least one tuned predetermined profile for a predetermined tuned exposure time or plurality of tuned exposure time sequences wherein said at least one tuned predetermined profile is comprised of a plurality of tuned predetermined figures of merit and is controllable through at least one of said plurality of tuned predetermined figures of merit, wherein said plurality of predetermined tuned figures of merit is comprised of a tuned B-Field magnitude, tuned rising slew rate, tuned rise time, tuned falling slew rate, tuned fall time, tuned frequency, tuned wavelength, and tuned duty cycle; controlling said at least one tuned time-varying stimulation field to produce said at least one tuned predetermined profile 12 by manipulating said tuned B-Field magnitude, said tuned exposure time or said plurality of tuned exposure time sequences and at least one of the following said tuned predetermined figures of merit: said tuned rising slew rate, said tuned rise time, said tuned falling slew rate, said tuned fall rime, said tuned frequency, said tuned wavelength, or said tuned duty cycle. The method may be further comprised of the step of tuning said at least one predetermined profile 50 associated with at least one time-varying stimulation field thereby resulting in at least one tuned time-varying stimulation field comprised of at least one tuned predetermined profile, wherein said at least one tuned predetermined profile is comprised of a plurality of tuned predetermined figures of merit and is controllable through at least one of said plurality of tuned predetermined figures of merit, wherein said plurality of predetermined tuned figures of merit is comprised of a tuned B-Field magnitude, tuned rising slew rate, tuned rise time, tuned falling slew rate, tuned fall time, tuned frequency, tuned wavelength, and tuned duty cycle.

Figure 8:
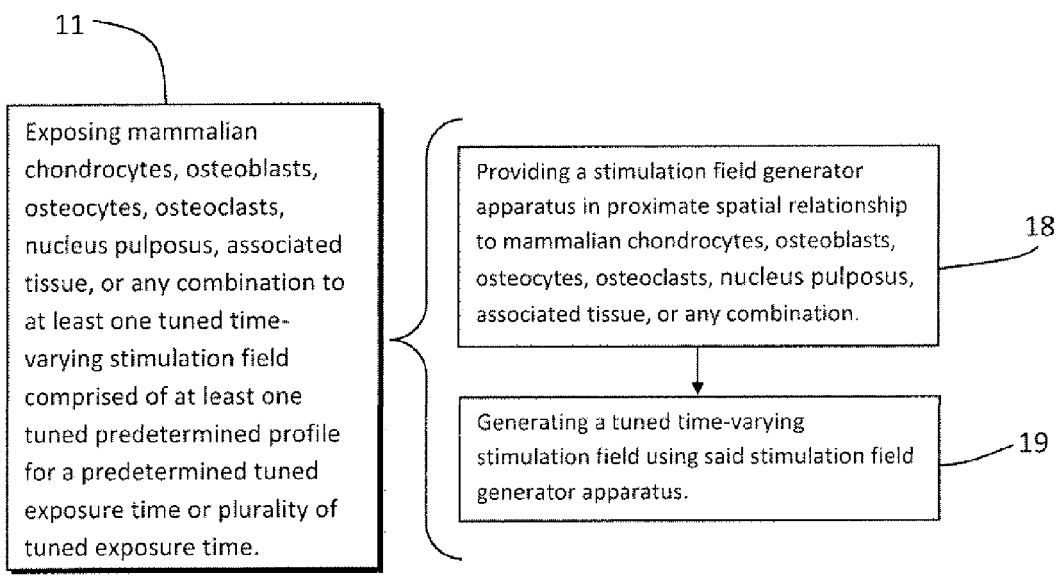
FIG. 8 depicts a flowchart of sub-steps associated with a step of exposing mammalian chondrocytes, osteoblasts, osteocytes, osteoclasts, nucleus pulposus, associated tissue, or any combination to at least one tuned time-varying stimulation field.

With particular reference to FIG. 8, for example, in an embodiment, the step of exposing said mammalian chondrocytes, osteoblasts, osteocytes, osteoclasts, nucleus pulposus, associated tissue, or any combination to at least one tuned time-varying stimulation field 11 may be comprised of: providing a stimulation field generator apparatus in proximate spatial relationship to said mammalian chondrocytes, osteoblasts, osteocytes, osteoclasts, nucleus pulposus, associated tissue, or any combination 18; and generating said tuned time-varying stimulation field using said stimulation field generator apparatus 19.

Figure 9:
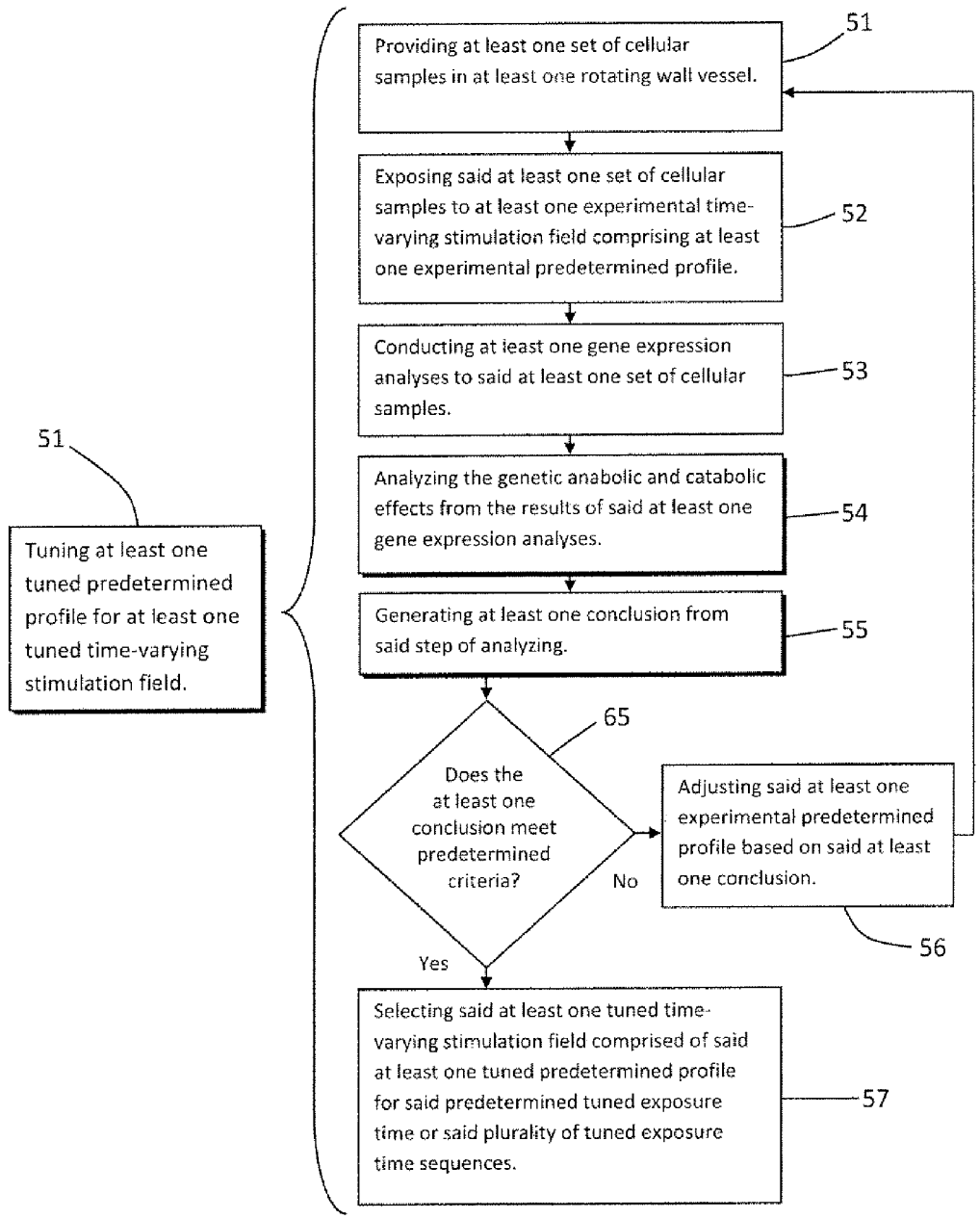
FIG. 9 depicts a flowchart of sub-steps associated with a step of tuning at least one tuned predetermined profile for at least one tuned time-varying stimulation field.

With particular reference to FIG. 9, for example, in an embodiment, the step of tuning may be comprised of: providing at least one set of cellular samples in at least one rotating wall vessel 51; exposing said at least one set of cellular samples 52 to at least one experimental time-varying stimulation field comprising at least one experimental predetermined profile; conducting at least one gene expression analyses to said at least one set of cellular samples 53; analyzing the genetic anabolic and catabolic effects from the results of said at least one gene expression analyses 54; generating at least one conclusion from said step of analyzing 55; adjusting said at least one experimental predetermined profile based on said at least one conclusion 56; and selecting at least one tuned time-varying stimulation field comprised of at least one tuned predetermined profile for a predetermined tuned exposure time or a plurality of tuned exposure time sequences 57. In an embodiment, the step of conducting at least one gene expression 53 may occur after said step of exposing said at least one set of cellular samples 52. In an embodiment, the step of adjusting said at least one experimental predetermined profile 56 may occur if said at least one conclusion does not meet predetermined criteria. The at least one set of cellular samples may be selected from the group consisting of human chondrocytes and human osteoblasts in addition to associated tissues.

Figure 10:
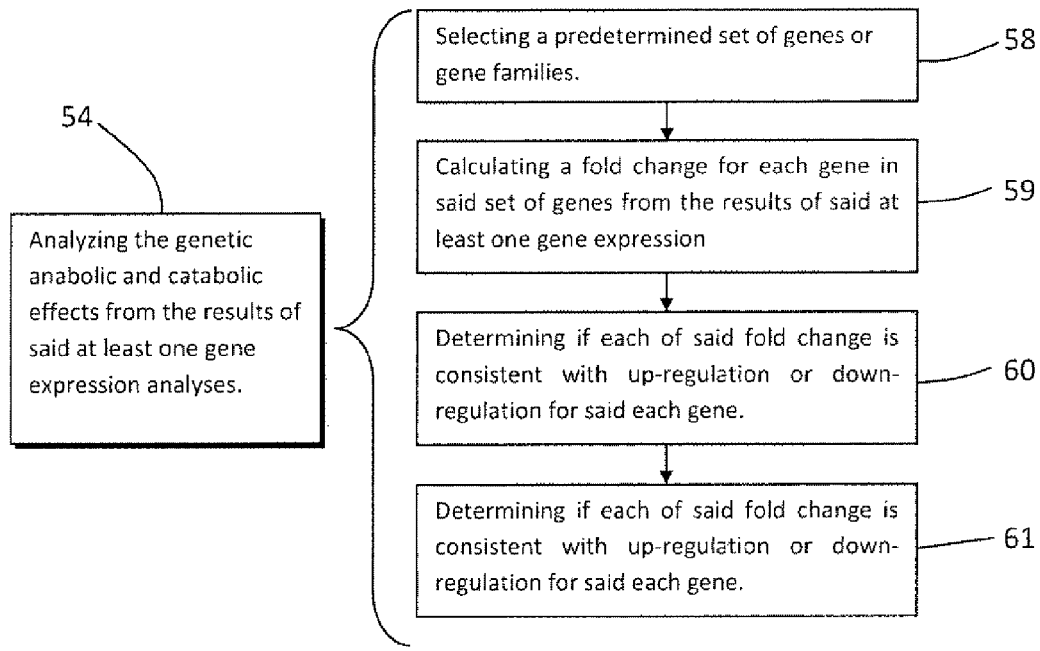
FIG. 10 depicts a flowchart of sub-steps associated with a step of analyzing genetic anabolic and catabolic effects from the results of at least one gene expression analyses.

With particular reference to FIG. 10, for example, in an embodiment, the step of analyzing the genetic anabolic and catabolic effects 54 may be comprised of: selecting a predetermined set of genes or gene families 58; calculating a fold change for each gene in said set of genes from the results of said at least one gene expression 59; determining if each of said fold change is consistent with up-regulation or down-regulation for said each gene 60; and classifying each of said fold change as an anabolic or catabolic effect based on said up-regulation or down-regulation for said each gene 61.

Figure 11:
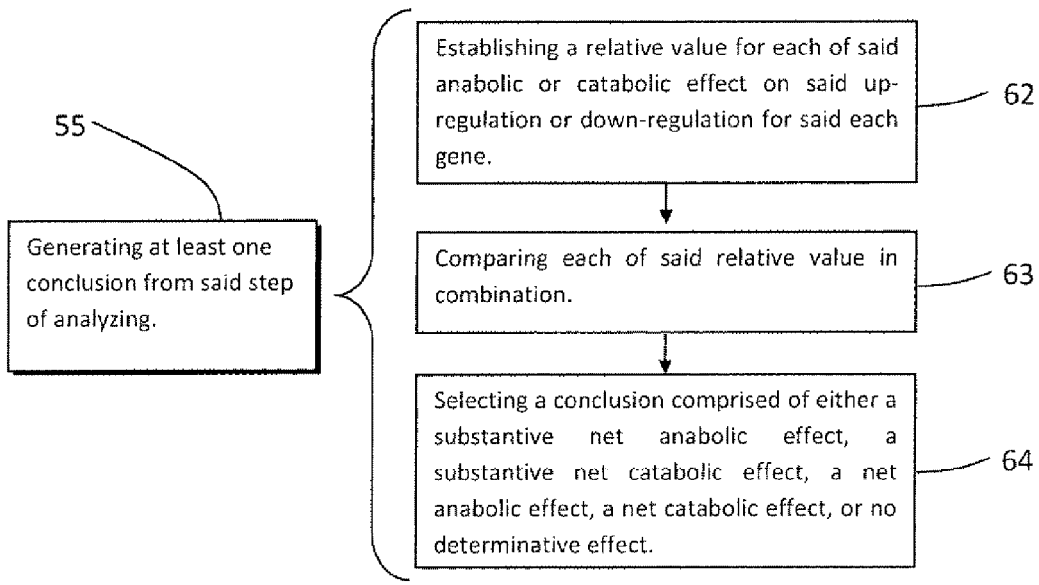
FIG. 11 depicts a flowchart of sub-steps associated with a step of generating at least one conclusion from a step of analyzing.

With particular reference to FIG. 11, for example, in an embodiment, the said step of generating at least one conclusion 55 may be comprised of: establishing a relative value for each of said anabolic or catabolic effect on said up-regulation or down-regulation for said each gene 62; comparing each of said relative value in combination 63; selecting a conclusion comprised of either a substantive net anabolic effect, a substantive net catabolic effect, a net anabolic effect, a net catabolic effect, or no determinative effect 64.

In an embodiment, a substantially square wave signal with a frequency from about 10 Hz to about 200 Hz can be induced to a ROI via a transmission component with the intent of influencing and thereby modifying the sub-cellular molecular components of mammalian chondrocytes, osteoblasts, osteocytes, osteoclasts, nucleus pulposus, (and associated tissue) thereby affecting the genomic and proteomic output or expression of these cells. The expression deltas are directly responsible, as compared to controls (untreated cells), for signaling differences at the sub-cellular and nuclear levels of the cells. The inventors have determined through laboratory tests that various embodiments of a stimulation field with a predetermined profile via manipulation of an electrical signal's FOMs, with specific ranges of electrical signal characteristics used to generate a stimulation field of predetermined profile, result in modification of cartilage and bone cells. For example, a time-varying stimulation field of predetermined profile comprised of a particular B-Field magnitude, frequency, rise time, fall time, slew rate, and wavelength for a predetermined exposure time or plurality of exposure time sequences (i.e., an exposure time schedule) may be used to preferentially excite specific sub-cellular organelles within the subject cells resulting in the desired events previously enumerated. The resultant profile may be a substantially square waveform.

Laboratory tests (discussed in more detail later) were comprised of exposing separate ROIs to a time-varying stimulation field of predetermined profile and a PEMF of predetermined profile wherein the ROIs was comprised of a rotating wall vessel (RWV). The RWV was inserted into a transmission component (see FIG. 5). The RWV contained a predetermined volume of microcarriers and predetermined cell volume comprised of human chondrocytes or human osteoblasts; and cell growth media. Both 2D and 3D culturing techniques were employed. Cell growth observations and analysis were then performed.

Stimulation Field Generator Apparatus

Figure 3:
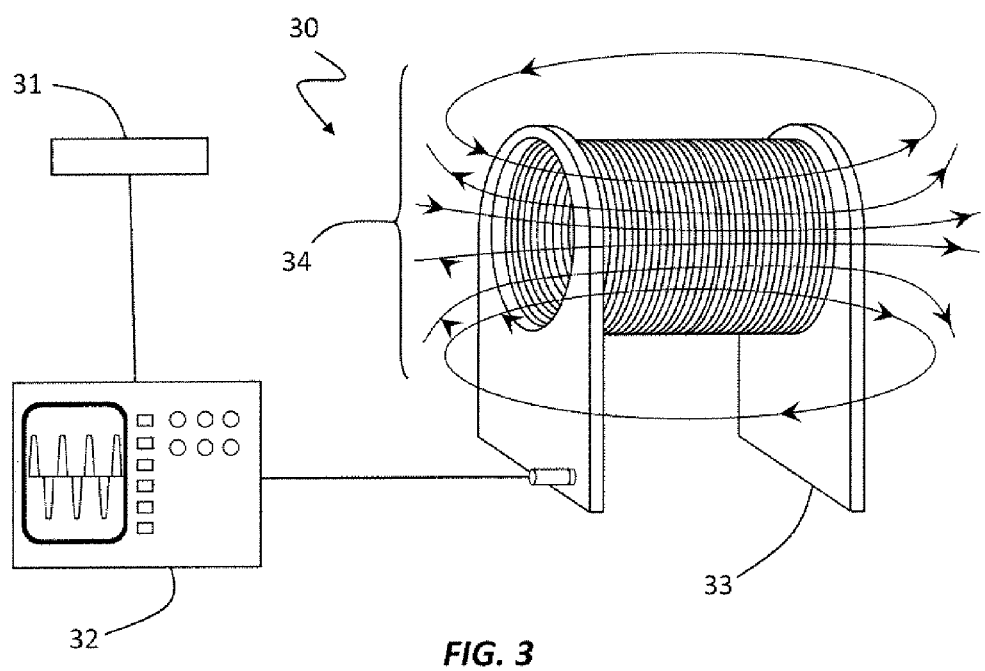
FIG. 3 illustrates an exemplary stimulation field generator apparatus.

With particular reference to FIG. 3, in regard to the stimulation field generator apparatus 30 mentioned above, an apparatus 30 is provided to electrically generate a stimulation field of predetermined profile 10. The apparatus 30 may include several components including: 1) a power source 31, 2) a control component 32, and 3) a transmission component 33. The apparatus 30 is effectively tuned via an electrical signal of predetermined profile to subsequently deliver a stimulation field of predetermined profile 10 to preferentially stimulate the biochemical cellular and sub-cellular molecular responses to trigger the activation of known mammalian genes responsible for the restoration, repair, maintenance, or any combination of cartilage and bone.

With continued reference to FIG. 3, the power source 31 supplies an electrical current to the control component 32 wherein the supplied electricity flows through the transmission component 33 thereby emitting a magnetic field 34. Multiple embodiments of a power source exist. For example, the power source 31 may comprise a battery; a power converter that converts one form of electrical power to another desired form and voltage (e.g., a device that converts 120 or 240 volt AC supplied by a utility company to a well-regulated lower voltage DC for electronic devices; low voltage, low power DC power supply units are commonly integrated with the devices they supply, such as computers and household electronics); a switched-mode power supply; a linear regulator, a rectifier; a high capacity capacitance power source; an electrical outlet power source; or any combination.

With continued reference to FIG. 3, the control component 32 of the apparatus 30 is used to produce a desired electrical signal, thereby in combination with the power source 31 and transmission component 33, produces a stimulation field of predetermined profile 10. The resultant stimulation field is further induced to a target tissue or ROI 21 by the transmission component 33, which will be discussed later. Multiple embodiments of a control component 32 exist. For example, the control component 32 may comprise a voltage or amperage driven signal generator as known as a function generator, arbitrary waveform generator, digital pattern generator, pulse generator, or frequency generator; computerized dongle circuitry with integrated firmware and software; a conductor; an amplifier; a sensor; a microprocessor; or any combination.

With continued reference to FIG. 3, the transmission component 33 delivers the stimulation field of predetermined profile to the target area in the proper field density. Multiple embodiments of a transmission component 33 are available. For example, in an embodiment, the transmission component 33 comprises a wire, wherein the wire is wound into a coil about a core, wherein the turns of the wire sit substantially side-by-side. When an electrical current is run through the wire, an electrically generated magnetic field or electromagnetic field passes through the center of the coil. An alternating current may be employed to thereby generate an electromagnetic field profile that alternates with respect to direction. Multiple embodiments exist in regard to the shape and design of the coil. For example, the coil may form the shape of a straight tube; a helix (similar to a corkscrew) such as a solenoid; a solenoid that is bent into a donut shape (i.e., a toroid); or any combination. The transmission component may also comprise a container of a predetermined shape and size wherein the wire is radially disposed on the container thereby forming the coil. Still further, in an embodiment, the transmission component may also comprise a sleeve 20 capable of wrapping around an appendage associated with a mammalian physiology wherein the ROI 21 is associated with said mammalian physiology.

Resultant Time-Varying B-Field

In an embodiment, the stimulation field generator apparatus 30 is tuned to deliver a stimulation field of predetermined profile 10 to preferentially stimulate the biochemical cellular and sub-cellular molecular responses to trigger the activation of known mammalian genes responsible for the restoration, repair, modification, and maintenance of cartilage and bone. Production of the desired profile is accomplished by controlling the electricity transferred within the stimulation field generator apparatus 30. As discussed previously, the electricity or electrical flow is controlled by the control component 32. The control component 32 manages the electricity in terms of an electrical signal. An electrical signal may be representative of a voltage, current, or both and conveys time-based information. Further, in an embodiment, additional management of the electrical signal may be conducted to normalize the total energy; to selectively modulate the resultant profile or waveform; to normalize the profile's duty cycle, rising slew rate, falling slew rate, etc.; or any combination.

With particular reference to FIG. 1, in an embodiment, a resultant simulation field of predetermined profile 10 is comprised of a substantially biphasic, square waveform. In an embodiment, a substantially biphasic, square waveform comprising a frequency in the range from about 9 Hz to about 200 Hz may be employed. Further, a resultant profile with the following FOMs may be employed: a B-Field magnitude from about 0.6 G to about 200 G; a rise time from about 125 µs to about 1 ms; a rising slew rate from about 2.0 kG/s to about 50.0 kG/s; a fall time from about 125 µs to about 1 ms; a falling slew rate from about 5.0 kG/s to about 50.0 kG/s; and a duty cycle of between 65-80% (and a subsequent dwell time of between 20-35%). Additional FOMs may be employed such as wavelength, exposure duration, etc. FIG. 1 illustrates a time-varying stimulation field profile for a stimulatory waveform for use in bone and tissue healing according to an embodiment of the present innovation.

Rotating Wall Vessels

Figure 4:
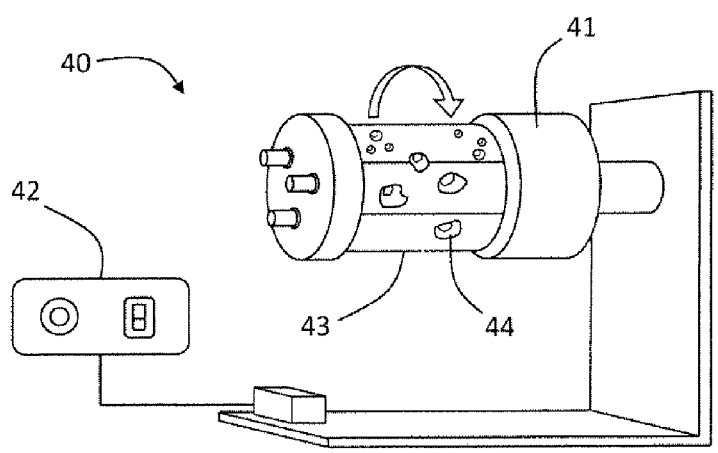
FIG. 4 illustrates an exemplary rotating wall vessel.

As described above and with particular reference to FIG. 4, RWVs 40 were used in laboratory experiments. Said RWVs are comprised of a base unit 41, a controller unit 42, and a culture vessel (aka vessel) 43. The RWV base unit 41 makes up the mechanical portion of the RWV 40. Briefly, the base unit contains a small air pump to provide circulation along the spin filter in the center of the culture vessel, and a stepper motor designed to spin the weight of all culture vessels. The RWV controller unit 42 houses electronics specifically created to energize the stepper motor within the base unit 41 to a consistent and calibrated rate, providing for equal rotation speeds between set ups so that each unit in service can be spun at identical rates. The RWV culture vessel 43 may be comprised of a Slow Turning Lateral Vessel (STLV) or a High Aspect Rotating Vessel (HARV). Cell samples 44 are contained in the culture vessel 43. Cell samples 44 may comprise chondrocytes, nucleus pulposus, osteoblasts, osteoclasts, osteocytes, associated tissue, or any combination. Each STLV is comprised of a base, a barrel, a center core for oxygenation, a cap with syringe ports, and a fill plug. To offset the potential damage to cells from off-gassing, new HARVs and STLVs must be rigorously detoxified in a procedure involving ethanol and autoclaving before first use.

Human Chondrocytes

In the laboratory tests, the HCH's were comprised of articular chondrocytes from donors ranging in age from 50-85, and both male and female donors. These are primary cell populations not established or immortalized cultures. Seven male lines and seven female lines were studied. Each individual donor was cultured in 2D and expanded until a minimum of $5 \times 10^7$ cells could be cryopreserved. Following initial, individual expansion, one vial of each donor was combined into a pool, keeping male donors separate from female donors, and expanded in 2D until an additional $1 \times 10^8$ cells in pool could be cryobanked. This combined pool never exceeded passage 7. One should not lose the primary characteristics of the cells in culture and therefore effort was expended into maximizing the number of cells available while minimizing the number of ex-vivo passages. Additionally, by banking as individuals first, then creating a pool, this technique provides the capability to "go back" and create additional vials of pooled cells if experimentation focus expands. The result of this effort was an additional 4.5×108 cells per sex or 9×108 total cells.

Human Osteoblasts

In laboratory testing, human osteoblasts (HOBS) were cryopreserved. Again, the HOBs were received from older donors, in this case ranging in age from 50 to 59 and from both male and female donors. Like the HCH, each lot/donor was expanded and banked as an individual, and then combined by sex into multi-donor pools, yielding a pool of five male donors and an additional pool of five female donors.

Cell Growth Media

Cell growth media, GTSF-2, was originally formulated at the National Aeronautics and Space Administration/Johnson Space Center by Dr. Goodwin with a U.S. patent issuing in 1998. (Goodwin, 1998) GTSF-2 is a tri-sugar, double-buffered media custom formulated on an L-15/Alpha-MEM base. Cells grown in two dimensions (2D) in standard flasks or plates are exposed to such an unnatural condition that their growth requirements are skewed as compared to in vivo. Hence, just about any glucose-containing, single-buffered isotonic salt solution will sustain them with minor exceptions as to primary, transformed, transfected or immortalized cell status. The RWV however creates a more in-vivo like environment. Cells are largely free from the pull of gravity and fluid shear, and are able to fully express their natural DNA encoded characteristics. That is, they are able to differentiate and develop cellular structures similar to or even exactly like their in-vivo counterparts. With a more complete growth capability, the need for a more complete media arises. GTSF-2 provides this complete media utilizing glucose, galactose and fructose as simple and increasingly complex energy sources, as well as HEPES and NaHCO3 (sodium bicarbonate) to ensure pH remains as close to physiologic normal as possible even in the most growth-active cultures. GTSF-2 is now available in several commercial formulations via their "specialty media" group as DPMI 40% MEM ALPHA MOD/60% L-15, catalog number SH3A099.01.

Two-Dimensional (2D) Culturing Techniques

In order to preserve as many vials of low passage cells as possible and extend the life of the cryo-pool of cells to accommodate any future needs, a single vial of frozen HCH or HOB pooled cells is thawed to initiate cells for bioreactor experiments. From a single 1×107 cells/vial unit, we are able to expand into as many as 2×108 cells, enough cells to populate twelve STLVs, without passage beyond p7. Standard culturing techniques are used. T-flasks purchased from Corning and GTSF-2 media with 10% FBS are used to expand the HOB or HCH cells sufficiently to meet the required numbers for the designed experiment. As the cell population within the flask reaches a cell density of approximately 75-80%, cells are passaged into a new flask using standard trypsinization techniques at a density roughly 25% of the previous flask. In other words, one flask is passaged into four. This continues until enough flasks are available to yield the necessary number of cells. It should be noted that continued growth of primary cells is difficult and time consuming as normal cells are not known to be sustained in 2D culture for prolonged periods.

Microcarrier Preparation

Several different microcarrier substrates are available in a variety of configurations to suit the need of the tissue being recapitulated. For example, PGA (polyglycolic acid), cyclodextran, collagen and gelatin are exemplary forms of microcarrier substrates. In an embodiment, gelatin microcarriers, commercially and readily available from Sigma-Aldrich (St. Louis, Mo.), called Cultispher were employed. Cultispher is a macroporous gelatin bead, coated with gelatin. Since the primary HCH and HOB are expensive and available in limited quantity, the increased surface area allows for better cell density with a lighter cell load. Cultispher is also fairly simple to use. It's provided as a dry powder and weighed out in milligrams based on the culture. Roughly 3 mg/ml into a 55 ml STLV is sufficient growth space for NCH and HOB cultures. Once the desired amount is weighed, the microcarriers are placed into a small, autoclavable jar and phosphate buffered saline (PBS) is added in sufficient quantity so that they can rehydrate properly. The microcarriers are allowed to "soak" in PBS overnight. The following day the microcarriers are autoclaved to ensure sterility. After autoclaving, they must be refrigerated overnight before use.

Initiation of Three-Dimensional (3D) Cultures

The quantity of cells and microcarriers used in any of the culture vessels is dependent on a number of factors. For the laboratory tests, the HCH and HOB are primary cells. As such they require a starting cell density considerably higher than that of a transformed or transfected cell lines. Additionally, in order for the RWV to work properly, cell density in relation to spatial and fluid limitations must be considered. The balance is adding enough cells for the crucial, initial cell-cell interactions that will establish the culture but not adding so many such that towards the end of the culture period the cell density is too great to be supported in the fluid volume and head space of the vessel. After a few limited trials, it was determined that an initial seeding density of 3) (1.05 cells/ml/vessel was a good balance for HCH and HOB cells. Using standard trypsinization techniques, the HCH or HOB cells were removed from the 2D flasks used to expand the HCH or HOB. The HCH or HOB cells were stored in media while performing cell counts. In an embodiment, hemacytometers and trypan exclusion techniques were used to determine cell counts. Once the number of cells per mL is determined, a predetermined amount of the cells were loaded into the vessel to equal the desired concentration. Next, pre-measured, pre-sterilized microcarriers were added. Finally, the remaining volume with GTSF2 media was added. After all culture components are loaded, air and all subsequent air bubbles were removed, and the vessel pressurized. This is accomplished via the syringe ports on the top of the vessel. By filling a syringe with media and repetitively squirting that media into the vessel while pulling air out, all dead/air space in the vessel can be filled. After all the bubbles have been removed in this manner, putting pressure on the fluid in the syringe creates pressure within the vessel. The vessels were subsequently pressurized and capped off. The vessel is now ready to be mounted on the base unit of the RWV.

3D Culture Maintenance

Generally speaking, the cultures are not fed within the first 48 hours after initiation. This allows the cells time to bind with the microcarriers and begin to produce the proteins responsible for cell-cell communication and adhesion. Feedings thereafter are determined via I-STAT® (Abbott Labs, Princeton, N.J.), a hand-held portable blood gas analyzer which is used in hospitals and clinics worldwide. The analysis it performs is dependent on the cartridge used. For culturing purposes, Na+ and Cl+ ions present in the supernatants are an indicator of cell metabolism in that NaCl is cleaved during uptake. Glucose is also notable. Glucose is one of three sugars in GTSF-2 and the only one that can currently be analyzed consistently. It is a primary energy source for the cells and the quantity used in any period of time between feedings provides information on the activity level of the cells. BUN (blood urea nitrogen) readings on the I-STAT® correlate with stress levels within the culture. $NaHCO_3$ (sodium bicarbonate) levels provide information about the quantity of acid produced as a result of metabolic activity. These various ions plus other parameters the I-STAT® measures, are essential to making good decisions as to quantity and frequency of feeding of the cultures. The ultimate goal is to maintain as physiologic normal within the bioreactor. A pH of 7.2, roughly 80-100 mg/dL of glucose, and adequate but not excessive salt and bicarbonate to balance the solution are achieved to maintain proper isotonicity. Deviations measured each 24 hour period from normal and the time it takes for them to occur is how the maintenance schedule for the cultures are determined.

Analytical Techniques Utilized Post-Experiment

Light microscopy is also used in conjunction with immunohistochemistry (IHC). Cells are embedded in a paraffin matrix, then thin layers are cut and mounted on slides. These slices are then stained with an antibody conjugated to a color of some kind or to a flourochrome to make the binding site visible. The antibodies can be to a cell type specific antigen found only in that specific cell. The antibodies can also be to a protein or cytokine product being produced by the cell. The slides with the tissue slices mounted on them are then viewed via a microscope—either light or confocal—and photographed for analysis and publication. Concentration of the color or flourochrome on the cell is indicative of the quantity of the antigen or protein in question. Dark coloring means high binding and high presence whereas light coloring is a reduced presence and low binding. IHC is generally considered a "qualitative" assessment however and other techniques are used to "quantify" marker expression. A portion of tissue like assemblies are aliquoted, washed 3× with filter-sterilized water, aspirated, and fixed in a final concentration of 2% Glutaraldehyde/3% Formaldehyde prepared in PBS. The samples are fixed for a minimum of 24 hrs at 4° C. overnight. The samples are flushed in triplicate with filter-sterilized deionized water to remove salts and then transferred for observation and imaging to a FEI XL30 Environmental Scanning Electron Microscope. Genetic array analyses are performed on experiments after each major change in parameters or change in cell type.

Laboratory Testing

Figure 5:
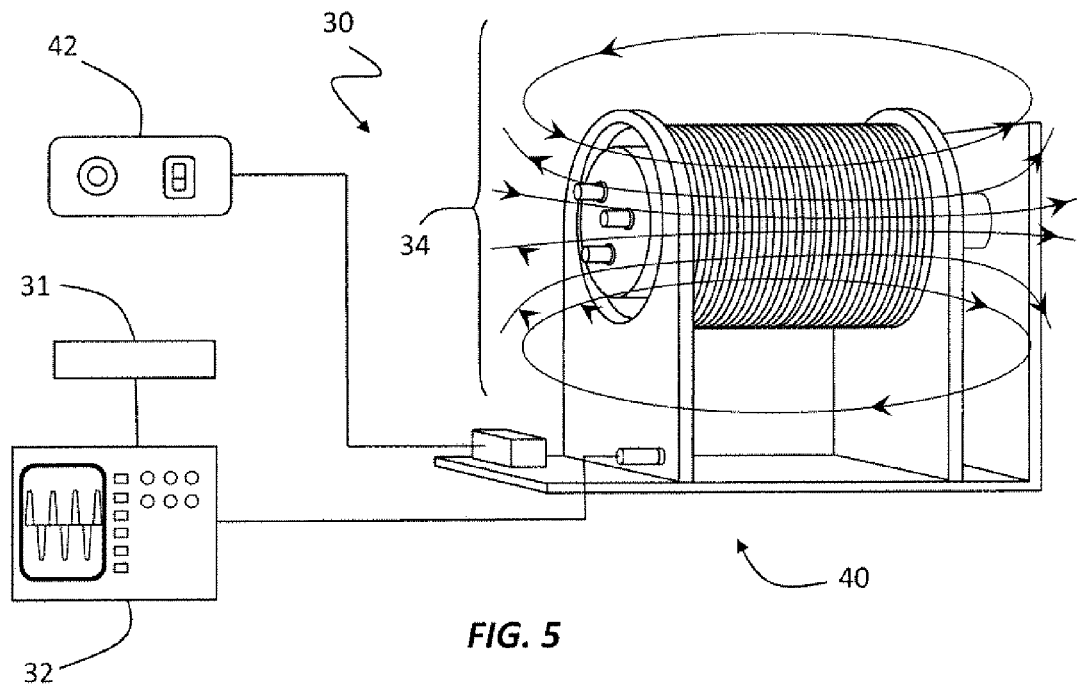
FIG. 5 illustrates an exemplary rotating wall vessel integrated with an exemplary stimulation field generator apparatus.
Figure 6:
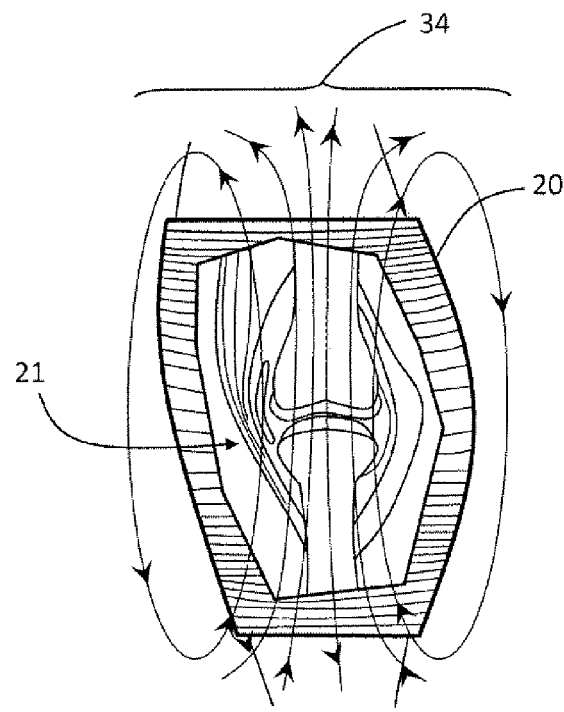
FIG. 6 illustrates an exemplary stimulation field generator apparatus in the form of a sleeve wherein said stimulation field generator apparatus delivers a magnetic field of predetermined profile to a region of interest on a mammalian physiology.

The inventors have conducted several experimental studies on the effects of time-varying stimulation fields on cellular processes. For example, in a study, a mixed population of human chondrocytes (HCH) was created and banked from patient samples ranging in age from 58 through 81 years. These samples were specifically selected due to their indications of early stage osteoarthritis. A male test population was exposed to a stimulation field of predetermined profiles comprising a predetermined B-Field magnitude and waveform shape, produced by an electrical signal in a continuous manner for about 30 days in a RWV. FIG. 5 illustrates an exemplary set-up incorporating the integration of a RWV and a stimulation field generator. Cellular gene expression analyses comprised of fold change analyses were accomplished by an AFFYMERIX® Gene Array survey of 47,000 human genes (U133 Plus 2.0 Chip) using the HCH samples exposed to the stimulation field as well as control HCH samples. The expression results were confirmed by a Reverse Transcriptase Polymerized Chain Reaction (RT-PCR) or LUMINEX® Assays. The inventors observed a difference between the types of regulated genes (discussed later). The inventors repeated the experiment, however, this time, two sets of HCH samples were each exposed to separate stimulation fields of predetermined profile (one stimulation field for each set of samples). The B-Field magnitude for each stimulation field was different in this experiment. After a similar gene array survey (described above), the inventors again observed a difference between the types of regulated genes exposed to the different stimulation fields. The inventors again repeated the experiment, however, this time; two HOB samples were exposed to separate stimulation fields of predetermined profile (one stimulation field for each set of samples). The B-Field magnitude for each stimulation field was substantially equal in this experiment. Due to a consensus in the related art, it was anticipated that any cellular activity, expressed in cellular gene expression analysis, would be relatively equal because the related art suggests that a B-Field's magnitude is the determinative variable. However, the experiment yielded unanticipated results. Specifically, a subsequent gene array survey revealed significant differences in gene expressions between the two cell samples. Also, the inventors observed for the third time differences in the type of regulated genes exposed to the different stimulation fields. As an example, the gene array survey results from these experiments indicate significant differences between stimulation field profiles in regard to potential use for osteoarthritis treatment. The results clearly indicate preferential regulation of cellular mechanisms identified with human chondrogenesis, osteogenesis, and extracellular matrix (ECM) deposition from a set of specific signals wherein B-Field magnitude is not the determinative variable. Rather, the shape of a stimulation field profile (i.e., waveform) and FOMs (in addition to a B-Field magnitude) are also influential factors.

In an embodiment, preparation of human chondrocytes was performed as follows: the mixed population of human chondrocytes described above was expanded in culture flasks. First, tissue-like-assemblies (TLAs) were constructed from normal human chondrocytes. From these TLAs, cell samples were grown (i.e., expanded) in two-dimensional (2D) culture flasks. The cell sample population was derived from several patient samples wherein these samples were pooled and gender isolated. The subsequent cultures were established in a GTSF-2 growth medium. GTSF-2 growth medium is a basal cell culture medium. In addition to traditional growth-factors, GTSF-2 contains a blend of three sugars (glucose, galactose, and fructose) at their physiological levels. The cultures were removed from the 2D flasks by trypsin-EDTA and counted.

Exposures of these chondrocyte cell samples to a predetermined time schedule of stimulation fields of predetermined profiles were performed in the following manner. A known cell volume was inoculated into at least three rotating wall vessels (RWVs) for each sample set and a control sample set wherein the RWVs are associated with a rotating bioreactor, such as a RCCS-1 system, which is a commercial unit manufactured by Synthecon, Inc. RWVs were inserted into a predetermined coil designed to deliver a stimulation field of predetermined profile comprised of a predetermined set of FOMs. The RWVs contained a predetermined volume of microcarriers. Electricity was subsequently supplied to the coil in accordance with a predetermined profile. In the simulated microgravity environment of the RWV, the human chondrocyte (HCH) and human osteoblasts (HOB) cells adhered to new growth matrices and began to multiply in cell-bead aggregates. The cell-bead aggregates were allowed to develop for a predetermined exposure time or plurality of exposure time sequences wherein multiple embodiments exist thereto (e.g., for about 30 days; between about 1 hour and about 720 hours; for 24 hours on, 24 hours off, repeat for a total of 30 days; etc.).

Cell growth observations and analyses were then performed using the sample set(s) which were contained in at least 3 RWVs per sample set and a control sample set also comprised of samples contained in at least 3 RWVs. Gene analyses were accomplished by an AFFYMETRIX® GENE-CHIP® Human Genome U133 Plus 2.0 Array, RT-PCR, or LUMINEX® Assay. A survey of the entire human genome of approximately 47,000 human genes exposed to multiple stimulation field profiles as regulated by multiple electrical signals was conducted.

Similar experiments were performed with human osteoblasts. In addition, the same result in regard to stimulation fields of different profiles inducing regenerative (e.g., anabolic) vs. reparative (e.g., catabolic) genes was observed but with increased genetic activity. A sample set of experimental results is as follows wherein said sample set are provided for the purpose of illustrating the development of the innovation as well as various embodiments of the innovation and are not meant to limit the present innovation in any fashion.

Example 1

Human Chondrocytes

In a first experiment, a first set of HCH cell samples contained in at least 3 RWVs were exposed to a first time-varying stimulation field of predetermined profile comprised of substantially a biphasic, square wave with a frequency of about 10 Hz; a wavelength of about 500 ms; a rising slew rate between about 0.2 T/s (2.0 kG/s) to about 0.45 T/s (4.5 kG/s); a falling slew rate between about 0.45 T/s (4.5 kG/s) to about 1.5 T/s (15.5 kG/s); a dwell time of about 10% after each burst; a duty cycle of about 80% on and about 20% off; and a resultant B-Field magnitude of about 5.9 µT (0.059 G). The experiment was conducted at 10 Hz. For reference purposes, the frequency of Earth's geomagnetic field is 7.83 Hz, thus the experiment satisfies the criteria of being appreciably different from the background magnetic field. Exposure was continuous for the length of this experiment wherein said length was about 30 days or about 720 hours. Gene analysis comprising a fold change analysis as describe above was conducted for the HCH cell samples exposed to the first time-varying stimulation field. Exemplary results from said gene analysis associated with the first time-varying stimulation field are provided in Table 2 below.

Generally, the related art consensus teaches that a field strength (either electric or magnetic) should be sufficiently powerful enough to penetrate deep enough inside cells to cause the desired effect. In order for this to happen the applied energy levels must be sufficiently high to penetrate deep enough inside cells, otherwise only a minimal and superficial effect can be expected. Electric fields are more susceptible to shielding effects as compared to magnetic fields. As described above, the laboratory set-up comprised the use of at least 3 RWVs for the first set of HCH samples wherein the at least 3 RWVs were each enclosed within wire coils designed to generate a magnetic field. Thus, the level of interference was minimized and the relatively low B-Field magnitude of the first time-varying stimulation field did result in the regulation of over 2000 genes. However, consideration as to applying an equivalent "effective" B-Field magnitude to a mammalian subject may require increasing the B-Field magnitude by a predetermined amplification factor of predetermined value or "gain" thereby requiring the creation of a dose response curve. This amplification factor or gain may be required due to differences in the level of interference associated with the inventors' laboratory set-up and a mammalian physiology (e.g., skeletal structure comprised of bone). The inventors stipulate that translation of the "optimum" effective field and conditions must take into account the systemic dampening encountered by the application to an entire physiology.

It is noted that an unanticipated observation was made in regard to the type of genes that were regulated. Specifically, the inventors discovered that genes normally associated with a regenerative function (i.e., anabolic genes) were up-regulated at a much higher percentage as compared to genes associated with a reparative function (i.e., catabolic genes). In some cases, genes exposed to the first time-varying stimulation field were down-regulated thereby resulting in a catabolic effect or up-regulated thereby resulting in an anabolic effect, or vice-versa. In an embodiment, a set of genes may be selected based on known function(s). The fold change for each gene is said set may be analyzed and determined to be consistent with up-regulation, down-regulation, or no regulation. Each regulated gene may be subsequently analyzed for an anabolic effect, catabolic effect, or no differential regulation (NOR). In a further embodiment, a relative value for each anabolic and catabolic effect may be assigned. And, the entire set of anabolic and catabolic effects may be compared in terms of the relative values of each effect. Thus, the resultant anabolic vs. catabolic effects may be determined. It should be noted that many of the genes (anabolic) up-regulated in this experiment are associated with embryonic development (Lanza, 2000). Table 1 provides a summary of said effects for the first experiment.

TABLE 1

| Stimulation Field | # Genes Regulated | # of Anabolic Gene Effects[†] | # of Catabolic Gene Effects[†] |
|---|---|---|---|
| First Time-Varying Stimulation Field | 2021 | 37 | 11 |

[†]In exemplary results in accordance to Table 1.

As can be observed in Table 1, the exemplary results for the first time-varying stimulation field are indicative of anabolic or regenerative effects. Table 2 provides additional details with respect to this observation wherein anabolic and catabolic effects are identified.

TABLE 2

| Gene Family | Fold Increase/Decrease for First Time-Varying Stimulation Field | Anabolic or Catabolic Effect of Genes Associated with Chondrocyte Development |
|---|---|---|
| WNT Family | | |
| WNT5B | +3.43 | Anabolic |
| WSP1 | +3.41 | Anabolic |
| WSP2 | +3.03 | Anabolic |
| Bone Morphogenetic Protein (BMP) Family | | |
| BMP2 | −8.63 | Catabolic |
| BMP6 | −4.56 | Catabolic |
| Forkhead Box (FOX) Family | | |
| FOXF1 | −3.32 | Catabolic |
| FOXN3 | −4.00 | Catabolic |
| Sex Determining Region Y (SRY) SOX Family | | |
| SOX9 (SRY-box 9) | −3.03 | Catabolic |
| SOX10 (SRY-box 10) | −2.91 | Catabolic |
| Parathyroid Hormone (PTH) Family | | |
| PTHLH (PTH-like hormone [LH]) | −11.00 | Catabolic |

TABLE 2-continued

| Gene Family | Fold Increase/Decrease for First Time-Varying Stimulation Field | Anabolic or Catabolic Effect of Genes Associated with Chondrocyte Development |
|---|---|---|
| Latent Transforming Growth Factor (TGF) Family (ECM) | | |
| Latent TGF Beta Binding Protein 2 | +6.54 | Anabolic |
| Latent TGF Beta Binding Protein 3 | +3.71 | Anabolic |
| Integrin Family (Cell Sulfur-Based [Sur]: ECM) | | |
| Integrin beta-like 1 (ITGBL1) with epidermal growth factor (EGF)-like repeat domains | +6.45 | Anabolic |
| Integrin beta 2 (ITGB2) complement component 3, receptor 3, and 4 subunit | +4.38 | Anabolic |
| Integrin beta 3 binding protein (beta3-endonexin) (ITGB3BP) | +2.93 | Anabolic |
| Interleukin (IL) Family (Cellular Cytokine Response) | | |
| IL-32 | +3.92 | Anabolic |
| IL-33 (IL-1 super family) | +3.39 | Anabolic |
| IL-1 receptor (IL-1R1) (IL-1 super family) | +2.95 | Anabolic |
| IL-4 inducible 1 (IL-4I1) (TH2 induction) | +3.01 | Anabolic |
| IL-8 | −4.82 | Anabolic |
| IL-6 | −2.66 | Anabolic |
| IL-24 | −3.41 | Catabolic |
| IL-17A | −2.87 | Anabolic |
| Thrombospondin Family (COMPs) | | |
| Thrombospondin 2 (THBS2) | +4.79 | Anabolic |
| Thrombospondin 3 (THBS3) | +3.73 | Anabolic |
| Laminin Family | | |
| Laminin Beta 1 (LAMB1) | +3.14 | Anabolic |
| Laminin Beta 2 (LAMB2) | +2.91 | Anabolic |
| Laminin Gamma 1 (LAMC1) | +2.82 | Anabolic |
| Proteoglycan Family | | |
| Biglycan (BGN) | +6.45 | Anabolic |
| Aggrecan (ACAN) | +3.81 | Anabolic |
| PAPLN (Papilin) | +3.38 | Anabolic |
| Chondroitin Sulphate Proteoglycan 4 (CSPG4) | +3.16 | Anabolic |
| Hyaluronan and Proteoglycan Link protein 1 (HAPLN 1) | +4.66 | Anabolic |
| Proteoglycan 4 (PRG4) | +2.85 | Anabolic |
| Collagen Family | | |
| Collagen, Type 1, Alpha 1 (COL1A1) | +32.67 | Anabolic |
| Collagen, Type 3, Alpha 1 (COL3A1) | +4.23 | Anabolic |
| Collagen, Type 4, Alpha 4 (COL4A4) | +3.53 | Anabolic |
| Collagen, Type 5, Alpha 1 (COL5A1) | +7.52 | Anabolic |
| Collagen, Type 5, Alpha 2 (COL5A2) | +6.54 | Anabolic |
| Collagen, Type 6, Alpha 2 (COL6A2) | +4.00 | Anabolic |
| Collagen, Type 8, Alpha 2 (COL8A2) | +3.63 | Anabolic |

TABLE 2-continued

| Gene Family | Fold Increase/Decrease for First Time-Varying Stimulation Field | Anabolic or Catabolic Effect of Genes Associated with Chondrocyte Development |
|---|---|---|
| Collagen, Type 12, Alpha 1 (COL12A1) | +3.93 | Anabolic |
| Collagen, Type 16, Alpha 1 (COL16A1) | +3.68 | Anabolic |
| Collagen, Type 21, Alpha 1 (COL21A1) | +5.54 | Anabolic |
| Collagen, Type 27, Alpha 1 (COL27A1) | +5.06 | Anabolic |
| Insulin (INS) Family | | |
| Insulin-Like Growth Factor (IGF) Binding Protein (BP) 1 | −13.18 | Catabolic |
| IGFBP5 | −5.03 | Catabolic |
| INS | −2.89 | Catabolic |

As can be observed in Table 2, several select genes of interest experienced up or down-regulation in the first experiment. For example, BMPs are a group of growth factors also known as cytokines originally discovered for their ability to induce the formation of bone and cartilage and are also considered to constitute a group of pivotal morphogenetic signals, orchestrating tissue architecture throughout the body. With specific reference to BMP2, BMP2 was down-regulated in the first experiment. BMP2 acts as a disulfide-linked homodimer and induces bone and cartilage formation and plays a key role in osteoblast differentiation. Further, BMP2 has been shown in clinical studies to be beneficial in the treatment of a variety of bone-related conditions including delayed union and non-union and has received FDA approval for clinical uses and is considered a repair or catabolic gene. In this experiment, the down-regulation of BMP2 represents a catabolic effect. Particularly as the goal was to enhance the growth of human chondrocytes. Also as will be seen in an experiment discussed later, a very similar application of a set of FOMs will result in the up-regulation of BMPs. Thus, this experiment demonstrated that changes in FOMs as well as overall B-Field can significantly change outcomes. As another example, collagen is a protein that strengthens and supports many tissues in the body, including cartilage, bone, tendon, and skin. Genes have been discovered that encode components of collagen. When these genes are up-regulated, an anabolic effect occurs. Conversely, when these genes are down-regulated, a catabolic effect occurs. In this experiment, the up-regulation of the genes in the collagen family represents an anabolic effect. It is noted that in some instances, the effects of up-regulation, down-regulation, or a combination of both of a gene; a combination of specific genes; a family of genes; a plurality of gene families can be substantive; or any combination can be substantive.

Example 2

Human Chondrocytes

Figure 2:
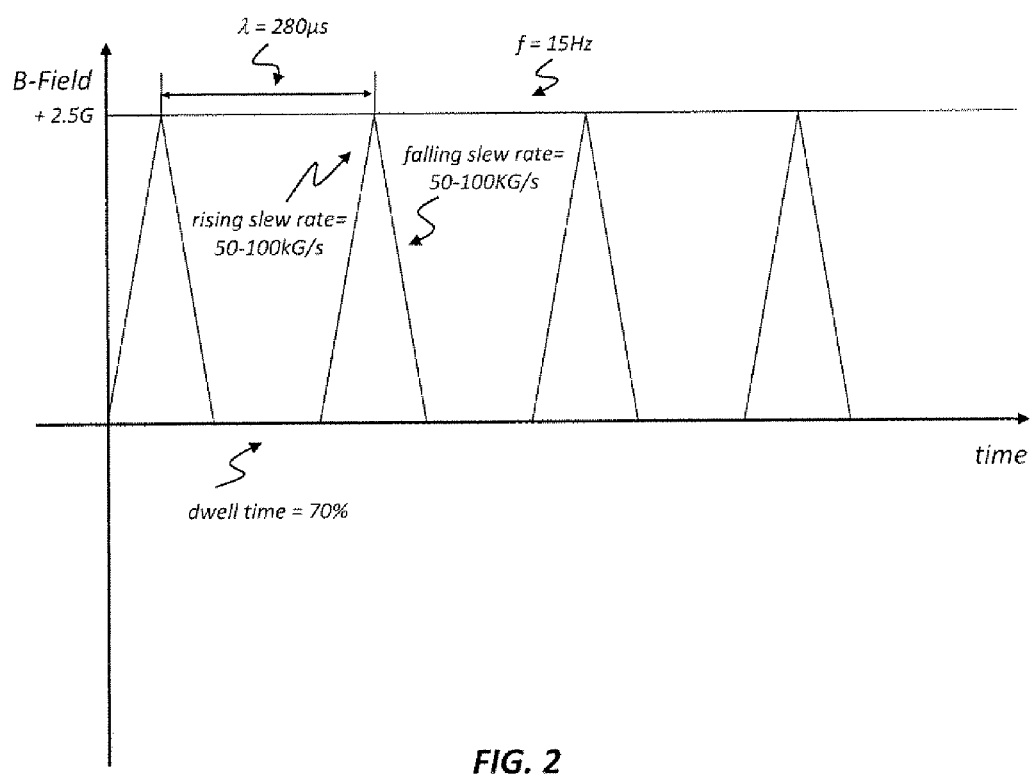
FIG. 2 depicts an exemplary stimulation field profile of a substantially monophasic, delta waveform.

In a second experiment, a second set of HCH cell samples contained in at least 3 RWVs were exposed to a second time-varying stimulation field of predetermined profile comprised of substantially a biphasic, square wave with a frequency of about 10 Hz; a wavelength of about 500 ms; a rising slew rate between about 0.2 T/s (2.0 kG/s) to about 0.45 T/s (4.5 kG/s); a falling slew rate between about 0.45 T/s (4.5 kG/s) to about 1.55 T/s (15.5 kG/s); a dwell time of about 10% after each burst; a duty cycle of about 80% on and about 20% off; and a resultant B-Field magnitude of about 65 µT (0.65 G). A third set of HCH cell samples contained in at least 3 RWVs were also separately exposed to a third time-varying stimulation field of predetermined profile comprised of a substantially monophasic, delta wave with a frequency of about 15 Hz; a duty cycle of about 30% on and about 70% off; and a resultant B-Field magnitude of about 250 µT (2.5 G). The third time-varying stimulation field is generally illustrated in FIG. 2. Note that the waveform represented in the third time-varying stimulation field may be designated a "pulse" or "burst" due to both its shape and wavelength (aka a "pulsed time-varying stimulation field"). Exposures were continuous for the length of this experiment wherein said length was about 30 days or about 720 hours. Equivalent equipment was used for the second and third sets of HCH cell samples. However, it is noted that different transmission components (e.g., antennae) were utilized between the first and second experiments.

These results were indicative of varying cellular effects due to substantive differences in the B-Field magnitudes with respect to the second and third time-varying stimulation fields as well as between the first and second time-varying stimulation fields. Hence, the results of the second experiment were, on its face, consistent with consensus related art publications that described a B-Field magnitude as comprising the determinative control factor for cellular effects. In other words, as can be observed in Table 4 and Table 2 (as compared to Table 4), there are substantive differences in the resultant gene expressions between human chondrocyte cellular exposure to the second and third time-varying stimulation fields as well as between the first and second time-varying stimulation fields. For example, the total number of regulated genes between the first and second time-varying stimulation fields (2021 vs. 1097) constituted a 46% decrease in regulated genes. It was not anticipated that such a substantive decrease in regulated genes would occur. Rather, because consensus related art publications disclose that a B-Field magnitude is the determinative control value and a high enough B-Field magnitude is required to stimulate cellular effects, it was anticipated that the total number of regulated genes would increase. The inventors hypothesized that the substantive decrease in regulated genes was related to the fact that different transmission components were used in regard to the first and second experiments. In terms of net effects, the results of the second experiment validated the inventors' observations in regard to anabolic vs. catabolic effects associated with the second time-varying stimulation field. Table 3 represents a summary of the second experiment in regard to gene expression.

TABLE 3

| Stimulation Field | # Genes Regulated | # of Anabolic Gene Effects* | # of Catabolic Gene Effects* |
|---|---|---|---|
| Second Time-Varying Stimulation Field | 1097 | 52 | 3 |
| Third Time-Varying Stimulation Field | 850 | 12 | 15 |

*In exemplary results in accordance to Table 4.

As can be observed in Table 3, when taking into account the exemplary results in accordance to Table 4, the anabolic and catabolic effects associated with the second and third time-varying stimulation fields are substantively different. Yet there is a commonality between the first and second stimulation fields or specifically, the disproportionally large number of anabolic vs. catabolic gene responses. The exemplary results for the second time-varying stimulation field are indicative of anabolic or regenerative effects. Conversely, the exemplary results from the third time-varying stimulation field are relatively neutral in regard to anabolic vs. catabolic effects while the total B-Field is much higher (65 µT vs. 250 µT). This result is not expected given prior art publications and was therefore unanticipated. Specifically there should be much greater effects at 250 µT as compared to 65 µT, however this was not the case. A comparison of the exemplary results associated with the two field profiles are provided in Table 4 below:

TABLE 4

| Gene Family | Fold Increase/Decrease for Second Time Varying Stimulation Field | Anabolic or Catabolic Effect of Genes Associated with Chondrocyte Development | Fold Increase/Decrease for Third Time Varying Stimulation Field | Anabolic or Catabolic Effect of Genes Associated with Chondrocyte Development |
|---|---|---|---|---|
| WNT Family | | | | |
| WNT5B | +00.0 | NDR | −3.43 | Catabolic |
| WSP1 | +00.0 | NDR | +3.25 | Anabolic |
| WSP2 | +00.0 | NDR | −2.91 | Catabolic |
| Bone Morphogenetic Protein (BMP) Family | | | | |
| BAMBI | +5.03 | Anabolic | +2.95 | Anabolic |
| BMP1 | +3.32 | Anabolic | −3.98 | Catabolic |
| BMP6 | +2.95 | Anabolic | +00.0 | NDR |
| Forkhead Box (FOX) Family | | | | |
| FOXQ1 | −4.69 | Catabolic | +00.0 | NDR |
| FOXN3 | −3.61 | Catabolic | +00.0 | NDR |
| FOXC1 | +00.0 | NDR | −3.32 | Catabolic |
| Sex Determining Region Y (SRY) SOX Family | | | | |
| SOX4 (SRY-box4) | +2.91 | Anabolic | +2.91 | Anabolic |
| SOX9 (SRY-box 9) | +00.0 | NDR | −4.66 | Catabolic |
| Parathyroid Hormone (PTH) Family | | | | |
| PTHLH (PTH-like hormone [LH]) | +4.03 | Catabolic | −6.59 | Anabolic |
| Transforming Growth Factor (TGF) Family | | | | |
| TGF-Beta 1 | +3.03 | Anabolic | +00.0 | NDR |
| TGF-Beta 2 | +4.41 | Anabolic | +00.0 | NDR |
| Latent TGF Beta Binding Protein 3 | +4.26 | Anabolic | +2.89 | Anabolic |
| Integrin Family (Cell Sur: ECM) | | | | |
| Integrin Alpha 8 (ITGA8) | +9.99 | Anabolic | +00.0 | NDR |
| Integrin Alpha 4 (ITGA4); CD49D | +4.41 | Anabolic | +00.0 | NDR |
| Integrin Alpha 6 ITGA6 | 0.00 | NDR | +3.23 | Anabolic |
| Integrin Beta 3 (ITGB3) | +3.63 | Anabolic | +00.0 | NDR |
| Integrin Beta 2 (ITGB2) | +3.71 | Anabolic | +00.0 | NDR |
| Integrin Alpha 2 (ITGA2); CD49B | +3.34 | Anabolic | +00.0 | NDR |
| Integrin beta-like 1 (ITGBL1) with epidermal growth factor (EGF)-like repeat domains | +5.46 | Anabolic | +00.0 | NDR |
| Interleukin Family (Cellular Cytokine Response) | | | | |
| Interleukin 33 (IL-33)(IL-1 super family) | $+8.74 \times 10^6$ | Anabolic | +00.0 | NDR |
| Interleukin 26 (IL-26)(IL-10 Family) | +4.59 | Anabolic | +00.0 | NDR |
| Interleukin 8 (IL-8) | +4.82 | Anabolic | +00.0 | NDR |
| Interleukin 6 (IL-6) | +2.89 | Anabolic | +00.0 | NDR |
| Interleukin (IL-11) | 0.00 | NDR | −2.91 | Catabolic |

TABLE 4-continued

| Gene Family | Fold Increase/ Decrease for Second Time Varying Stimulation Field | Anabolic or Catabolic Effect of Genes Associated with Chondrocyte Development | Fold Increase/ Decrease for Third Time Varying Stimulation Field | Anabolic or Catabolic Effect of Genes Associated with Chondrocyte Development |
|---|---|---|---|---|
| Thrombospondin Family | | | | |
| Thrombospondin 1 (THBS1) | +4.61 | Anabolic | +00.0 | NDR |
| Thrombospondin 2 (THBS2) | +3.73 | Anabolic | +00.0 | NDR |
| ADAM metallopeptidase with thrombospondin type 1 motif (ADAMTS1) | +3.18 | Anabolic | −3.72 | Catabolic |
| ADAM metallopeptidase with thrombospondin type 5 motif (ADAMTS5) | +4.00 | Anabolic | −2.89 | Catabolic |
| Laminin Family | | | | |
| Laminin Beta 1 (LAMB1) | +00.0 | NDR | +3.78 | Anabolic |
| Proteoglycan Family | | | | |
| Biglycan (BGN) | +3.46 | Anabolic | +00.0 | NDR |
| Aggrecan (ALAN) | +3.81 | Anabolic | +00.0 | NDR |
| PAPLN (Papilin) | +00.0 | NDR | +4.79 | Anabolic |
| Hyaluronan and Proteoglycan Link protein 1 (HAPLN 1) | +5.03 | Anabolic | +00.0 | NDR |
| Proteoglycan 4 (PRG4) | +3.76 | Anabolic | +00.0 | NDR |
| Leucine Proline-enriched Proteoglycan (Leprecan-Like) 1 (LEPRE1) | +2.91 | Anabolic | +00.0 | NDR |
| Matrix Metallapeptidase (MMP) Family | | | | |
| SMMP1 (interstitial collagenase) | −3.39 | Anabolic | +5.50 | Catabolic |
| MMP3 (interstitial collagenase) stromelysin 1 | −2.89 | Anabolic | +3.18 | Catabolic |
| MMP13 (interstitial collagenase 3) | −3.97 | Anabolic | +4.41 | Catabolic |
| Tissue Inhibitor of Metalloproteinases (TIMP) Family | | | | |
| TIMP Inhibitor 3 (TIMP3) (Sorsby Fundus Dystrophy) | +3.03 | Anabolic | −4.03 | Catabolic |
| Collagen Family | | | | |
| Collagen, Type 1, Alpha 1 (COL1A1) | +32.62 | Anabolic | +5.98 | Anabolic |
| Collagen, Type 3, Alpha 1 (COL3A1) | +4.23 | Anabolic | +3.84 | Anabolic |
| Collagen, Type 4, Alpha 1 (COL4A1) | +2.95 | Anabolic | +00.0 | NDR |
| Collagen, Type 4, Alpha 2 (COL4A2) | +3.12 | Anabolic | +00.0 | NDR |
| Collagen, Type 4, Alpha 4 (COL4A4) | +5.06 | Anabolic | +00.0 | NDR |
| Collagen, Type 5, Alpha 1 (COL5A1) | +22.62 | Anabolic | +00.0 | NDR |
| Collagen, Type 11, Alpha 1 (COL11A1) (Cartilage) | +44.63 | Anabolic | +00.0 | NDR |
| Collagen, Type 12, Alpha 1 (COL12A1) | +3.92 | Anabolic | +00.0 | NDR |
| Collagen, Type 15, Alpha 1 (COL15A1) (Muscle and Microvascular Deterio) | +22.47 | Anabolic | −9.71 | Catabolic |
| Collagen, Type 21, Alpha 1 (COL21A1) | +00.0 | NDR | +5.06 | Anabolic |
| Collagen, Type 27, Alpha 1 (COL27A1) | +00.0 | NDR | +5.06 | Anabolic |
| Insulin Family | | | | |
| Insulin-Like Growth Factor (IGF) 1 (IGF1) | 0.00 | NDR | +3.94 | Anabolic |
| Insulin-Like Growth Factor (IGF) 2 (IGF2) | +4.76 | Anabolic | +4.29 | Anabolic |

TABLE 4-continued

| Gene Family | Fold Increase/ Decrease for Second Time Varying Stimulation Field | Anabolic or Catabolic Effect of Genes Associated with Chondrocyte Development | Fold Increase/ Decrease for Third Time Varying Stimulation Field | Anabolic or Catabolic Effect of Genes Associated with Chondrocyte Development |
|---|---|---|---|---|
| IGF Binding Protein (IGFBP) 1 | +7.78 | Anabolic | −52.35 | Catabolic |
| IGFBP2 | +13.45 | Anabolic | −00.0 | NDR |
| IGFBP3 | +10.70 | Anabolic | −3.07 | Catabolic |
| IGFBP5 | +2.81 | Anabolic | −5.74 | Catabolic |
| IGFBP6 | 0.00 | NDR | −3.05 | Catabolic |
| Actin Family | | | | |
| Actin, Alpha 2 (ACTA) 2 | +3.32 | Anabolic | +00.0 | NDR |
| Actinin, Alpha 1 (ACTN1) | +3.12 | Anabolic | +00.0 | NDR |
| Palladin Cytoskeletal Associated Protein (PALLD) | +3.23 | Anabolic | +00.0 | NDR |
| Actin/Cytoskeletal Related Genes | | | | |
| Cytoskeleton-Associated Protein (CKAP) 4 | +2.85 | Anabolic | +00.0 | NDR |
| Catenin (Cadherin-Associated Protein, Alpha 1) (CTNNA1) | +3.81 | Anabolic | +00.0 | NDR |
| Cadherin 2, N-Cadherin (Neuronal) (CDH2) | +16.45 | Anabolic | +00.0 | NDR |
| H-Cadherin (Heart) (CDH13) | +3.27 | Anabolic | −2.99 | Catabolic |
| Filamin B, Beta (Actin Binding Protein 278) (FLNB) | +2.95 | Anabolic | +00.0 | NDR |
| Filamin C, Gamma (Actin Binding Protein 280) (FLNC) | +00.0 | NDR | −2.93 | Catabolic |

As can be observed in Table 4, several select genes of interest experienced up or down-regulation in the second experiment. It is noted that ADAMTS genes are generally considered to be anabolic when up-regulated but catabolic when down-regulated. As can be observed in Table 4, ADAMTS1 and 5 were both up-regulated with respect to exposure to the second time-varying stimulation field. Conversely, ADAMTS1 and 5 were down-regulated with respect to exposure to the third time-varying stimulation field. MMPs proteases are generally considered catabolic because they break down tissue (a process associated with remodeling and repair). When MMPs are down-regulated, catabolic effects are suppressed thereby having in a net anabolic effect. Conversely, when MMPs are up-regulated their catabolic effects are enhanced. As can be observed in Table 4, MMPI, 3, and 13 were down-regulated with respect to exposure to the second time-varying stimulation field. Conversely, MMP 1, 3, and 13 were up-regulated with respect to exposure to the third time-varying stimulation field. The functionality of BMPs was discussed above. With particular reference to BMP1, it is a metalloprotease that acts on procollagen I, II, and III. BMP1 is involved in cartilage development and is related to a regenerative function or anabolic in nature. As can be observed in Table 4, BMP1 was up-regulated with respect to exposure to the second time-varying stimulation field. Conversely, BMP1 was down-regulated with respect to exposure to the third time-varying stimulation field.

Example 3

Human Osteoblasts

In a third experiment, a first set of HOB cell samples contained in at least 3 RWVs were exposed to substantially the same time-varying stimulation field profile as compared to the second time-varying stimulation field of predetermined profile in the second experiment. For clarity purposes, this stimulation field profile will be referred to as a fourth time-varying stimulation field of predetermined profile comprised of substantially a biphasic, square wave with a frequency of about 10 Hz; a wavelength of about 500 ms; a rising slew rate between about 0.2 T/s (2.0 kG/s) to about 0.45 T/s (4.5 kG/s); a falling slew rate between about 0.45 T/s (4.5 kG/s) to about 1.55 T/s (15.5 kG/s); a dwell time of about 10% after each burst; a duty cycle of about 80% on and about 20% off; and a resultant B-Field magnitude of about 65 µT (0.65 G). A second set of HOB cell samples contained in at least 3 RWVs were also separately exposed to substantially the same stimulation field as compared to the third time-varying stimulation field previously described. For clarity purposes, this pulsed stimulation field will be referred to as the fifth time-varying stimulation field of predetermined profile comprised substantially of a monophasic, delta wave with a frequency of 15 Hz; a duty cycle of about 30% on and about 70% off; and a resultant B-Field magnitude of about 65 µT (0.65 G), wherein said B-Field magnitude is substantially fixed in one direction (i.e., monophasic). Note that in this experiment, the B-Field magnitudes of the fourth and fifth time-varying stimulation fields were substantially equal. Equivalent equipment was used for the first and second sets of HOB cell samples. It is also noted that equivalent equipment was used in comparison with the second and third experiments. Exposures were continuous for the length of this experiment wherein said length was about 30 days or about 720 hours. As in the second experiment, the resultant cellular effects between the first and second sets of HOB cell samples were substantively different. It is noted here that two separate gene analyses for the first and second set of HOB cell samples were conducted. For the first set of HOB cell samples, these gene analyses are defined as #1 and #2 Fold Increase/Decrease for Fourth Time Varying Stimulation Field in Tables 6 and 7 below. For the second set of HOB cell samples, these gene analyses are defined as #3 and #4 Fold Increase/Decrease for Fifth Time Varying Stimulation Field in Tables 6 and 7 below. A comparison of exemplary results associated with the two separate gene analyses for each of the two field profiles are provided in the tables below:

TABLE 5

| Stimulation Field | # Genes Regulated | # of Anabolic Gene Effects^ | # of Catabolic Gene Effects^ |
|---|---|---|---|
| #1 Fourth Time-Varying Stimulation Field | 2495 | 87 | 6 |
| #2 Fourth Time-Varying Stimulation Field | 2691 | 81 | 4 |
| #3 Fifth Time-Varying Stimulation Field | 437 | 20 | 7 |
| #4 Fifth Time-Varying Stimulation Field | 527 | 21 | 5 |

^In exemplary results in accordance to Tables 6 and 7.

TABLE 6

| Gene Family | #1 Fold Increase/Decrease for Fourth Time Varying Stimulation Field | Anabolic or Catabolic Effect Effect of Genes Associated with Osteoblast and bone cell Development | #3 Fold Increase/Decrease for Fifth Time Varying Stimulation Field | Anabolic or Catabolic Effect Effect of Genes Associated with Osteoblast and bone cell Development |
|---|---|---|---|---|
| actin (ACTS) | NDR | NRE | +3.3309 | Anabolic |
| ADAM metallopeptidase domain 10 (ADAM10) | +4.0239 | Anabolic | +3.1776 | Anabolic |
| ADAM metallopeptidase domain 17 (tumor necrosis factor interacts with TNF alpha (ADAM17) | +3.1086 | Anabolic | NDR | NRE |
| ADAM metallopeptidase with thrombospondin type 1 motif (ADAMTS1) | +9.6955 | Anabolic | NDR | NRE |
| apoptosis inhibitor 5 (API5) | +2.9426 | Anabolic | NDR | NRE |
| B-cell CLL/lymphoma 3 (BCL3) | +2.9013 | Anabolic | NDR | NRE |
| B-cell CLL/lymphoma 6 (zinc finger protein 51) (BCL6) | NDR | NRE | +2.8595 | Anabolic |
| BCL2-associated athanogene 2 (BAG2) | NDR | NRE | +2.8730 | Anabolic |
| BCL2-related protein A1 (BCL2A1) | −3.2422 | Catabolic | NDR | NRE |
| biglycan (BGN) (201262_s_at) | +17.3408 | Anabolic | NDR | NRE |
| bone morphogenetic protein 2 (BMP2) | +136.2100 | Anabolic | NDR | NRE |
| bone morphogenetic protein receptor (BMPR2) | +3.2517 | Anabolic | NDR | NRE |
| cadherin 11 Bone Specific/Osteoblasts (CDH11) | +3.4967 | Anabolic | NDR | NRE |
| Calcium/calmodulin-dependent protein kinase (CaM kinase) ∥ delta (CAMK2D) | +6.0076 | Anabolic | NDR | NRE |
| calmodulin 1 (phosphorylase kinase (CALM1) | NDR | NRE | +2.9689 | Anabolic |
| calumenin (CALU) (214845_s_at) | +4.0815 | Anabolic | +3.5804 | Anabolic |
| cartilage oligomeric matrix protein (COMP) | +12.1656 | Anabolic | −3.8106 | Catabolic |
| CASP8 and FADD-like apoptosis regulator (CFLAR) | −2.8575 | Anabolic | NDR | NRE |

TABLE 6-continued

| Gene Family | #1 Fold Increase/Decrease for Fourth Time Varying Stimulation Field | Anabolic or Catabolic Effect Effect of Genes Associated with Osteoblast and bone cell Development | #3 Fold Increase/Decrease for Fifth Time Varying Stimulation Field | Anabolic or Catabolic Effect Effect of Genes Associated with Osteoblast and bone cell Development |
|---|---|---|---|---|
| catenin (cadherin-associated protein) (CTNNB1) | +4.4593 | Anabolic | +3.2564 | Anabolic |
| cathepsin C (CTSC) | −4.2881 | Anabolic | NDR | NRE |
| cathespin O (CTSO) | −2.8365 | Anabolic | NDR | NRE |
| cathespin S (CTSS) | −2.9715 | Anabolic | NDR | NRE |
| chondroitin sulfate proteoglycan 4 (CSPG4) (214297_at) | +4.0672 | Anabolic | NDR | NRE |
| clusterin Anti apoptosis and MMPs (CLU) | +19.4810 | Anabolic | NDR | NRE |
| collagen (COL12A1) | +2.9218 | Anabolic | NDR | NRE |
| collagen (COL15A1) | −16.2926 | Anabolic | NDR | NRE |
| collagen (COL1A1) | +2.8683 | Anabolic | NDR | NRE |
| collagen (COL3A1) | +4.7532 | Anabolic | NDR | NRE |
| collagen (COL3A1) | +4.5715 | Anabolic | NDR | NRE |
| collagen (COL4A1) | +3.1465 | Anabolic | NDR | NRE |
| collagen (COL4A2) | +3.2012 | Anabolic | +2.8581 | Anabolic |
| collagen (COL4A3BP) | +3.3796 | Anabolic | NDR | NRE |
| collagen (COL5A2) | +3.6551 | Anabolic | NDR | NRE |
| collagen (COL6A1) | +3.0345 | Anabolic | +3.2741 | Anabolic |
| collagen (COL8A1) | +2.9195 | Anabolic | NDR | NRE |
| cytochrome P450 (CYP1B1) embryonic development | +6.4062 | Anabolic | +3.7186 | Anabolic |
| cytochrome P450 (CYP24A1) Vit D3 homeostatis | +5.0863 | Anabolic | NDR | NRE |
| endoglin (Osler-Rendu-Weber syndrome 1) (ENG) | NDR | NRE | +2.9135 | Catabolic |
| Fas (TNF receptor superfamily (FAS) | +3.2724 | Anabolic | +3.5713 | Anabolic |
| fibrillin 1 (FBN1) | +3.2809 | Anabolic | +3.7335 | Anabolic |
| fibroblast growth factor 1 (acidic) (FGF1) | −2.8473 | Anabolic | NDR | NRE |
| fibroblast growth factor 18/ embryonic development, cell growth, morphogenesis, tissue repair (FGF18) | +4.5734 | Anabolic | NDR | NRE |
| fibulin 1 (FBLN1) | +4.1863 | Anabolic | NDR | NRE |
| forkhead box N3 (FOXN3) | +3.9116 | Anabolic | NDR | NRE |
| forkhead box O1 (FOXO1) | +2.8822 | Anabolic | NDR | NRE |
| forkhead box O3 Tumor Suppressor (FOXO3) (204132_s_at) | +3.3640 | Anabolic | NDR | NRE |
| forkhead box O3 (FOXO3) (210655_s_at) | +3.1184 | Anabolic | NDR | NRE |
| forkhead box Q1 Function Unknown (FOXQ1) | +3.3091 | Anabolic | NDR | NRE |
| importin 11 (IPO11) | +2.9481 | Anabolic | NDR | NRE |
| importin 7 (IPO7) (200992_at) | +4.7592 | Anabolic | NDR | NRE |
| insulin-like growth factor 1 (somatomedin C) (IGF1) | +3.1870 | Anabolic | NDR | NRE |
| insulin-like growth factor binding protein 1 (IGFBP1) | −13.6898 | Anabolic | NDR | NRE |
| insulin-like growth factor binding protein 5 (IGFBP5) | −18.5362 | Anabolic | NDR | NRE |
| interleukin 1 family (IL1F8) | NDR | NRE | +4.1682 | Catabolic |
| interleukin 17D (IL17D) | −2.8729 | Anabolic | NDR | NRE |
| interleukin 32 (IL32) | +2.8646 | Anabolic | NDR | NRE |

TABLE 6-continued

| Gene Family | #1 Fold Increase/Decrease for Fourth Time Varying Stimulation Field | Anabolic or Catabolic Effect Effect of Genes Associated with Osteoblast and bone cell Development | #3 Fold Increase/Decrease for Fifth Time Varying Stimulation Field | Anabolic or Catabolic Effect Effect of Genes Associated with Osteoblast and bone cell Development |
|---|---|---|---|---|
| interleukin 33 (IL33) | +48.2994 | Anabolic | +3.2614 | Anabolic |
| interleukin 6 (interferon (IL6) | −3.7429 | Anabolic | NDR | NRE |
| interleukin 8 (IL8) | +3.0542 | Anabolic | +3.6065 | Anabolic |
| laminin (LAMB1) | +2.9398 | Anabolic | −2.9140 | Catabolic |
| leptin (obesity homolog (LEP) | −2.8863 | Anabolic | NDR | NRE |
| matrix metallopeptidase 14 (membrane-inserted) (MMP14) | NDR | NRE | +2.8543 | Catabolic |
| mitogen-activated protein kinase associated protein 1 (MAPKAP1) | +3.6457 | Anabolic | NDR | NRE |
| mitogen-activated protein kinase-activated protein kinase 2/ inhibition of apoptosis, regulation of cell development, and cell differentiation (MAPKAPK2) | +8.9929 | Anabolic | NDR | NRE |
| msh homeobox 1 (MSX1) | +3.4459 | Anabolic | NDR | NRE |
| Notch homolog 2 (*Drosophila*) (NOTCH2) | +5.1985 | Anabolic | +3.6551 | Anabolic |
| nuclear factor of activated T-cells (NFATC3) | +4.0922 | Anabolic | NDR | NRE |
| osteoglycin (OGN) | +3.2508 | Anabolic | NDR | NRE |
| pallidin homolog (mouse) (PLDN) | +2.9546 | Anabolic | NDR | NRE |
| parathyroid hormone-like hormone (PTHLH) | −3.9816 | Catabolic | NDR | NRE |
| peroxisome proliferator-activated receptor alpha (PPARA) | +3.7661 | Anabolic | NDR | NRE |
| platelet derived growth factor C (PDGFC) | +11.8582 | Anabolic | +3.7643 | Anabolic |
| procollagen-lysine (PLOD2) | +3.1194 | Anabolic | NDR | NRE |
| procollagen-proline (P4HB) | +3.1958 | Anabolic | +3.3121 | Anabolic |
| protocadherin beta 6 (PCDHB6) | +3.5486 | Anabolic | NDR | NRE |
| protocadherin gamma subfamily A (PCDHGA3) | +3.1857 | Anabolic | NDR | NRE |
| reticulocalbin 1 (RCN1) | −2.8536 | Anabolic | NDR | NRE |
| runt-related transcription factor 2 (RUNX2) | +4.2303 | Anabolic | NDR | NRE |
| signal transducer and activator of transcription 1 (STAT1) | −4.7015 | Anabolic | +3.0161 | Catabolic |
| signal transducer and activator of transcription 2 (STAT2) | −3.1518 | Anabolic | NDR | NRE |
| signal transducer and activator of transcription 3 (acute-phase response factor) (STAT3) | +2.9537 | Anabolic | NDR | NRE |
| SMAD family member 1 (SMAD1) | +2.9000 | Anabolic | NDR | NRE |
| SMAD family member 2 (SMAD2) | +2.9848 | Anabolic | NDR | NRE |
| SMAD family member 4 (SMAD4) | +4.8768 | Anabolic | +2.9077 | Anabolic |
| SMAD family member 6 (SMAD6) | +3.6075 | Anabolic | NDR | NRE |
| sparc/osteonectin (SPOCK1) | +3.3007 | Anabolic | NDR | NRE |

TABLE 6-continued

| Gene Family | #1 Fold Increase/Decrease for Fourth Time Varying Stimulation Field | Anabolic or Catabolic Effect Effect of Genes Associated with Osteoblast and bone cell Development | #3 Fold Increase/Decrease for Fifth Time Varying Stimulation Field | Anabolic or Catabolic Effect Effect of Genes Associated with Osteoblast and bone cell Development |
|---|---|---|---|---|
| SRY (sex determining region Y)-box 4 (SOX4) (201417_at) | +6.0198 | Anabolic | NDR | NRE |
| SRY (sex determining region Y)-box 9 (campomelic dysplasia (SOX9) | +2.9461 | Anabolic | NDR | NRE |
| stanniocalcin 1 (STC1) | −133.3427 | Anabolic | NDR | NRE |
| stanniocalcin 2 (STC2) | −6.3031 | Anabolic | −2.8380 | Anabolic |
| superoxide dismutase 2 (SOD2) | +4.1182 | Anabolic | NDR | NRE |
| syndecan 1 (SDC1) | +2.8761 | Anabolic | NDR | NRE |
| TRAF family member-associated NFKB activator (TANK) | +2.9982 | Anabolic | NDR | NRE |
| tumor necrosis factor (ligand) superfamily TRAIL (TNFSF10) | −5.8708 | Anabolic | NDR | NRE |
| tumor necrosis factor (ligand) superfamily (TNFSF13B) | −3.9019 | Anabolic | +3.3676 | Catabolic |
| tumor necrosis factor (ligand) superfamily (TNFSF15) | −13.4107 | Anabolic | NDR | NRE |
| tumor necrosis factor receptor superfamily (TNFRSF10D) | NDR | NRE | −2.9040 | Anabolic |
| v-akt murine thymoma viral oncogene homolog 3 (protein kinase B (AKT3) | +4.3325 | Anabolic | NDR | NRE |

TABLE 7

| Gene Family | #2 Fold Increase/Decrease for Fourth Time Varying Stimulation Field | Anabolic or Catabolic Effect Effect of Genes Associated with Osteoblast and bone cell Development | #4 Fold Increase/Decrease for Fifth Time Varying Stimulation Field | Anabolic or Catabolic Effect Effect of Genes Associated with Osteoblast and bone cell Development |
|---|---|---|---|---|
| actin (ACTB) | NDR | NRE | +3.2497 | Anabolic |
| ADAM metallopeptidase domain 10 (ADAM10) | +3.8784 | Anabolic | +3.1870 | Anabolic |
| ADAM metallopeptidase domain 17 (tumor necrosis factor (ADAM17) | +3.0926 | Anabolic | +3.1296 | Anabolic |
| ADAM metallopeptidase domain 33 (ADAM33) | −5.5601 | Catabolic | NDR | NRE |
| ADAM metallopeptidase with thrombospondin type 1 motif (ADAMTS1) | +4.3910 | Anabolic | NDR | NRE |
| ADAM metallopeptidase with thrombospondin type 1 motif (ADAMTS6) | −2.9113 | Catabolic | NDR | NRE |
| B-cell CLL/lymphoma 6 (zinc finger protein 51) (BCL6) | +4.2264 | Anabolic | +2.9836 | Anabolic |
| biglycan (BGN) | +10.8190 | Anabolic | NDR | NRE |
| bone gamma-carboxyglutamate (gla) protein (osteocalcin) (BGLAP) | +3.4068 | Anabolic | NDR | NRE |
| bone morphogenetic protein 2 (BMP2) | +265.1634 | Anabolic | NDR | NRE |

TABLE 7-continued

| Gene Family | #2 Fold Increase/Decrease for Fourth Time Varying Stimulation Field | Anabolic or Catabolic Effect Effect of Genes Associated with Osteoblast and bone cell Development | #4 Fold Increase/Decrease for Fifth Time Varying Stimulation Field | Anabolic or Catabolic Effect Effect of Genes Associated with Osteoblast and bone cell Development |
|---|---|---|---|---|
| calcium/calmodulin-dependent protein kinase (CaM kinase) II delta (CAMK2D) | +4.2280 | Anabolic | NDR | NRE |
| calmodulin 1 (phosphorylase kinase (CALM1) | NDR | NRE | +2.9379 | Anabolic |
| calumenin (CALU) | +3.2043 | Anabolic | +3.1993 | Anabolic |
| cartilage oligomeric matrix protein (COMP) | +17.7007 | Anabolic | −4.0956 | Catabolic |
| catenin (cadherin-associated protein) (CTNNB1) | +4.5090 | Anabolic | +3.5238 | Anabolic |
| cathepsin C (CTSC) | −4.9355 | Anabolic | NDR | NRE |
| cathepsin H (CTSH) | −3.1342 | Anabolic | NDR | NRE |
| cathepsin S (CTSS) | −2.8325 | Anabolic | NDR | NRE |
| chondroitin sulfate proteoglycan 4 (CSPG4) | +3.2199 | Anabolic | NDR | NRE |
| clusterin (CLU) | +26.2849 | Anabolic | NDR | NRE |
| collagen (COL12A1) | +3.6143 | Anabolic | +2.9117 | Anabolic |
| collagen (COL16A1) | −2.8512 | Anabolic | −3.0354 | Anabolic |
| collagen (COL1A1) | +2.8438 | Anabolic | NDR | NRE |
| collagen (COL3A1) | +5.4512 | Anabolic | NDR | NRE |
| collagen (COL4A2) | +3.0110 | Anabolic | NDR | NRE |
| collagen (COL5A2) | +2.9639 | Anabolic | NDR | NRE |
| cytochrome P450 (CYP11A1) | −2.9175 | Anabolic | NDR | NRE |
| cytochrome P450 (CYP19A1) | −11.9176 | Anabolic | NDR | NRE |
| cytochrome P450 (CYP1B1) | +7.1220 | Anabolic | +4.4823 | Anabolic |
| cytochrome P450 (CYP24A1) | +5.3640 | Anabolic | NDR | NRE |
| cytochrome P450 (CYP4V2) | −2.9432 | Anabolic | NDR | NRE |
| cytochrome P450 (CYP51A1) | +4.7959 | Anabolic | NDR | NRE |
| cytochrome P450 (CYP7B1) | −4.6752 | Anabolic | NDR | NRE |
| endoglin (Osler-Rendu-Weber syndrome 1) (ENG) | +2.9055 | Catabolic | NDR | NRE |
| Fas (TNF receptor superfamily (FAS) | +3.0606 | Anabolic | NDR | NRE |
| fibrillin 1 (FBN1) | +3.3971 | Anabolic | +3.6475 | Anabolic |
| fibroblast growth factor 1 (acidic) (FGF1) | −2.9045 | Anabolic | NDR | NRE |
| fibroblast growth factor 18 (FGF18) embryonic development | +6.0853 | Anabolic | NDR | NRE |
| fibulin 1 (FBLN1) | +4.8829 | Anabolic | NDR | NRE |
| forkhead box Q1 (FOXQ1) | +3.2639 | Anabolic | NDR | NRE |
| importin 11 (IPO11) | +3.5238 | Anabolic | NDR | NRE |
| importin 7 (IPO7) | +4.7773 | Anabolic | NDR | NRE |
| insulin-like growth factor 1 (somatomedin C) (IGF1) | +2.9529 | Anabolic | NDR | NRE |
| insulin-like growth factor binding protein 1 (IGFBP1) | −11.3487 | Anabolic | NDR | NRE |
| insulin-like growth factor binding protein 2 (IGFBP2) | −3.4126 | Anabolic | NDR | NRE |
| interleukin 1 family (IL1F8) | NDR | NRE | +4.6908 | |
| interleukin 32 (IL32) | +2.8329 | Anabolic | NDR | NRE |
| interleukin 33 (IL33) | +77.4903 | Anabolic | +3.4328 | Anabolic |
| interleukin 4 induced 1 (IL4I1) | −2.9266 | Anabolic | NDR | NRE |

TABLE 7-continued

| Gene Family | #2 Fold Increase/Decrease for Fourth Time Varying Stimulation Field | Anabolic or Catabolic Effect Effect of Genes Associated with Osteoblast and bone cell Development | #4 Fold Increase/Decrease for Fifth Time Varying Stimulation Field | Anabolic or Catabolic Effect Effect of Genes Associated with Osteoblast and bone cell Development |
|---|---|---|---|---|
| interleukin 6 (interferon (IL6) | −4.0698 | Anabolic | NDR | NRE |
| interleukin 8 (IL8) | NDR | NRE | +4.4075 | Anabolic |
| laminin (LAMB1) | +3.5168 | Anabolic | NDR | NRE |
| leptin (obesity homolog (LEP) | −2.8432 | Anabolic | NDR | NRE |
| mitogen-activated protein kinase associated protein 1 (MAPKAP1) | +3.4504 | Anabolic | NDR | NRE |
| mitogen-activated protein kinase-activated protein kinase 2 (MAPKAPK2) | +6.6319 | Anabolic | +3.4968 | Anabolic |
| msh homeobox 1 (MSX1) | +3.1872 | Anabolic | NDR | NRE |
| Notch homolog 2 (Drosophila) (NOTCH2) | +6.6681 | Anabolic | +3.9031 | Anabolic |
| nuclear factor of activated T-cells (NFATC3) | +4.4679 | Anabolic | NDR | NRE |
| osteoglycin (OGN) | +2.9048 | | NDR | NRE |
| pallidin homolog (mouse) (PLDN) | +3.7839 | | NDR | NRE |
| parathyroid hormone-like hormone (PTHLH) | −2.9471 | Anabolic | NDR | NRE |
| peroxisome proliferator-activated receptor alpha (PPARA) | +3.3980 | Anabolic | NDR | NRE |
| platelet derived growth factor C (PDGFC) (222719_s_at) | +8.6547 | Anabolic | NDR | NRE |
| platelet-derived growth factor alpha polypeptide (PDGFA) | +2.8343 | Anabolic | NDR | NRE |
| procollagen-lysine (PLOD2) | +3.2120 | Anabolic | NDR | NRE |
| procollagen-proline (P4HB) | +3.3854 | Anabolic | +3.2322 | Anabolic |
| protocadherin 7 (PCDH7) | +4.3290 | Anabolic | NDR | NRE |
| protocadherin beta 15 (PCDHB15) | +3.1245 | Anabolic | NDR | NRE |
| protocadherin beta 5 (PCDHB5) | +4.9055 | Anabolic | NDR | NRE |
| protocadherin gamma subfamily A (PCDHGA10/// PCDHGA11/// PCDHGA12/// PCDHGA3/// PCDHGA5/// PCDHGA6) | +3.6665 | Anabolic | +3.1682 | Anabolic |
| protocadherin gamma subfamily C (PCDHGC3) | +3.2147 | Anabolic | NDR | NRE |
| runt-related transcription factor 2 (RUNX2) | +4.6912 | Anabolic | NDR | NRE |
| signal transducer and activator of transcription 1 (STAT1) | −5.6924 | Anabolic | +3.5656 | Catabolic |
| signal transducer and activator of transcription 2 (STAT2) | −3.1503 | Anabolic | +3.3033 | Catabolic |
| signal transducer and activator of transcription 3 (acute-phase response factor) (STAT3) | +2.8810 | Anabolic | +2.8416 | Anabolic |
| SMAD family member 2 (SMAD2) | +2.9680 | Anabolic | NDR | NRE |
| SMAD family member 4 (SMAD4) | +4.4233 | Anabolic | +3.2649 | Anabolic |
| SMAD family member 6 (SMAD6) | +3.8208 | Anabolic | NDR | NRE |

TABLE 7-continued

| Gene Family | #2 Fold Increase/Decrease for Fourth Time Varying Stimulation Field | Anabolic or Catabolic Effect Effect of Genes Associated with Osteoblast and bone cell Development | #4 Fold Increase/Decrease for Fifth Time Varying Stimulation Field | Anabolic or Catabolic Effect Effect of Genes Associated with Osteoblast and bone cell Development |
|---|---|---|---|---|
| SMAD family member 7 (SMAD7) | +3.4806 | Anabolic | NDR | NRE |
| sparc/osteonectin (SPOCK1) | +3.2869 | Anabolic | NDR | NRE |
| SRY (sex determining region Y)-box 4 (SOX4) | +3.6585 | Anabolic | NDR | NRE |
| SRY (sex determining region Y)-box 9 (campomelic dysplasia (SOX9) | +2.8642 | Anabolic | NDR | NRE |
| stanniocalcin 1 (STC1) | −76.1478 | Anabolic | NDR | NRE |
| stanniocalcin 2 (STC2) | −7.3838 | Anabolic | NDR | NRE |
| superoxide dismutase 2 (SOD2) | +3.6248 | Anabolic | NDR | NRE |
| syndecan 1 (SDC1) | +3.0232 | Anabolic | NDR | NRE |
| TIMP metallopeptidase inhibitor 3 (Sorsby fundus dystrophy (TIMP3) | NDR | NRE | +2.8771 | Anabolic |
| tumor necrosis factor (ligand) superfamily BAFF (TNFSF13B) | −3.1995 | Anabolic | NDR | NRE |
| tumor necrosis factor (ligand) superfamily TRAIL (TNFSF10) | −3.2316 | Anabolic | +3.6523 | Catabolic |
| tumor necrosis factor receptor superfamily (TNFRSF10A) | +2.8649 | Anabolic | NDR | NRE |
| tumor necrosis factor receptor superfamily (TNFRSF10D) | NDR | NRE | −2.9102 | Anabolic |
| tumor necrosis factor receptor superfamily (TNFRSF11B) | −2.9260 | Catabolic | NDR | NRE |
| tumor necrosis factor receptor superfamily (TNFRSF21) | NDR | NRE | +3.4511 | Catabolic |
| v-akt murine thymoma viral oncogene homolog 3 (protein kinase B (AKT3) | +4.0693 | Anabolic | NDR | NRE |

Based on consensus related art publications, it was anticipated that the results associated with the fourth and fifth time-varying stimulation fields would be substantially or at least reasonably equal given that the B-Field magnitudes were substantially the same. However, the actual results refuted this expectation. In fact, the actual results of the third experiment indicate that the differences in gene expressions were not substantially the result of B-Field magnitude. Rather, other FOMs related to a field's profile affect cellular activity wherein said other FOMs can overcome the strength (or lack thereof) of a B-Field magnitude. It is noted that of the 47,000 genes analyzed, approximately 2500 genes responded to the fourth time-varying stimulation field as compared to approximately 450 genes responding to the fifth time-varying stimulation field which comprises a greater than 550% increase in gene response. The difference in the number of gene responses and associated percentage difference is indicative of the fourth time-varying stimulation field having a significantly greater effect on HOBs as compared to the fifth time-varying stimulation field. Hence, as previously discussed, the results refute the related art expectation that substantially or at least reasonably similar results were expected due to substantially similar B-Field magnitudes associated with the fourth and fifth time-varying stimulation fields.

It is also noted that the same observation with regard to regulation of regenerative vs. reparative genes in the first and second experiments was made in this experiment. In sum, it can be stated that certain types of genes and genomic cascades respond differently to different stimulation fields of predetermined profiles. And, in regard to the fourth time-varying stimulation field, anabolic genes are substantially up-regulated as compared to other types of genes. Further, the inventors realized another unanticipated result wherein the inventors observed that the percentage of regulated genes associated with the HOB sample exposed to the fourth time-varying stimulation field was much higher as compared to the percentage of regulated genes associated with the HCH sample exposed to the second time-varying stimulation field (note: as stated before, the second and fourth time-varying stimulation fields are substantially equal). In other words, the inventors observed that the same stimulation field of predetermined profile affects genetic response in HCH differently as compared to HOB. Thus, the same stimulation field profile can be applied to different tissue wherein different results occur. In regard to different genetic responses in HCH and compared to HOB, the inventors postulate that due to substantial differences in the total CA2+ and K+ density in cartilage vs. mineralized bone, the subcellular transcription signals are different when exposed to the same stimulation field. This presents an unanticipated explanation for the many different results seen in scientific articles using PEMFs. Thus a variety of potential tuning solutions for different mammalian tissues is likely.

Still further, the inventors realized that based on the fact that different stimulation fields can affect cells with regard to regulation of regenerative and reparative genes to produce a net regenerative (i.e., anabolic) or net reparative (i.e., catabolic) effect, different stimulation fields and their associated exposure times or time schedules can be used in combination with each other to design customized therapeutic applications. Multiple embodiments exist for combining stimulation fields and their associated exposure times or time schedules. For example, in an embodiment, a stimulation field (and its associated exposure times or time schedules) tuned to produce a net catabolic effect in HOB cells, HCH cells, or both can be initially used to stimulate a net catabolic effect. After a predetermined amount of catabolic or reparative effect(s) are realized, another stimulation field (and its associated exposure times or time schedules) tuned to produce a net anabolic effect in HOB cells, HCH cells, or both can be utilized until a predetermined amount of anabolic or regenerative effect(s) are realized. The process can be repeated if so desired. Alternatively, in another embodiment, it is conceivable that a therapeutic application may be customized to use a stimulation field (and its associated exposure times or time schedules) tuned to produce a net catabolic effect in HOB cells, HCH cells, or both in combination and simultaneously with a stimulation field (and its associated exposure times or time schedules) tuned to produce a net anabolic effect in HOB cells, HCH cells, or both. Still further, the use of tuned stimulation fields in series, in parallel, or both may be employed.

The experiments discussed above and associated results represent a means to tune at least one predetermined profile of a time-varying stimulation field to preferentially stimulate (up-regulate, down-regulate, or a combination of both) the biochemical cellular and sub-cellular molecular responses to trigger the activation of known mammalian genes responsible for the restoration, repair, and maintenance of cartilage and bone. Specifically, said preferential stimulation can be targeted to specific genes, gene families, or a combination of both, responsible for anabolic effects, catabolic effects, or a combination of both. Tables 2, 4, 6, and 7 are incorporated herein as identifying examples of such specific genes and gene families that may be targeted for preferential stimulation by a tuned time-varying stimulation field of at least one tuned predetermined profile. It has been demonstrated that the use of cell samples (such as HOB or HCH, however any kind of biological cell sample can be used depending on the biological matter of interest) and microcarriers encased in RWVs in combination with a stimulation field generator can be used in an empirical manner to tune a time-varying stimulation field of at least one predetermined profile to optimize genetic anabolic effects, catabolic effect, or a combination of both. With particular reference to FIG. 9, for example, as can be extracted by the sequence of experiments previously described, a tuning step 50 may comprise providing at least one set of cellular samples in at least one rotating wall vessel 51; exposing said at least one set of cellular samples to at least one experimental time-varying stimulation field comprising at least one experimental predetermined profile 52; conducting at least one gene expression analyses to said at least one set of cellular samples 53; analyzing the genetic anabolic and catabolic effects from the results of said at least one gene expression analyses 54; generating at least one conclusion from said step of analyzing 55; comparing said at least one conclusion with predetermined criteria 65; if said at least one conclusion does not meet predetermined criteria, adjusting said at least one experimental predetermined profile based on said at least one conclusion 56; and selecting said at least one tuned time-varying stimulation field profile for said predetermined tuned exposure time or said plurality of tuned exposure time sequences 57. The predetermined criteria in step 56 may comprise, for example, a predetermined number of anabolic genetic effects or responses; catabolic genetic effects or responses; or a combination of both. With particular reference to FIG. 10, for example, the step of analyzing the genetic anabolic and catabolic effects may be comprised of: selecting a predetermined set of genes 58; calculating a fold change for each gene in said set of genes from the results of said at least one gene expression 59; determining if each of said fold change is consistent with up-regulation or down-regulation for said each gene 60; and classifying each of said fold change as an anabolic or catabolic effect based on said up-regulation or down-regulation for said each gene 61. The said step of generating at least one conclusion may be comprised of: establishing a relative value for each of said anabolic or catabolic effect on said up-regulation or down-regulation for said each gene 62; comparing each of said relative value in combination 63; selecting a conclusion comprised of either a substantive net anabolic effect, a substantive net catabolic effect, a net anabolic effect, a net catabolic effect, or no determinative effect 64.

One skilled in the art would readily appreciate that the present innovation is well adapted to carry out the objects and obtain the ends and advantages mentioned, as well as those inherent therein. The present examples along with the methods, procedures, treatments, and biological materials described herein are presently representative of embodiments and preferred embodiments; are exemplary; and are not intended as limitations to the scope of the innovation. Changes therein and other uses will occur to those skilled in the art which are encompassed within the spirit of the subject innovation as defined by the scope of the claims.

WORKS CITED

Atkins, G. (2009). Vitamin K promotes mineralization, osteoblast to osteocyte transition and an anti-catabolic phenotype by γ-carboxylation dependent and independent mechanisms. *American Journal of Physiology—Cell Physiology,* 1152.

Bone, (2010, July). Retrieved Jul. 26, 2010, from Wikipedia: en.wikipedia.org/wiki/Bone Cartilage, (2010, July). Retrieved Jul. 26, 2010, from Wikipedia: en.wikipedia.org/wiki/Cartilage de Bolster, M. (1997). *Glossary of Terms Used in Bioinorganic Chemistry.* Retrieved Oct. 30, 2007, from Glossary of Terms Used in Bioinorganic Chemistry: chem.qmul.ac.uktiupacibioinorg/AB.html#20

Goodwin, T. J. (1998). U.S. Pat. No. 5,846,807. United States of America.

Goodwin, T. J., & Parker, C. R. (2007). U.S. Pat. No. 7,179, 217. United States of America.

Ishikawa, T. (2006). Steroid and Xenobiotic Receptor SXR Mediates Vitamin K2-activated Transcription of Extracellular Matrix-related Genesand Collagen Accumulation in Osteoblastic Cells. Journal of Biological Chemistry, 16927-16934.

Koshihara, Y. (1997). Vitamin K2 Enhances Osteocalcin Accumulation in the Extracellular Matrix of Human Osteoblasts In Vitro. *Journal of Bone and Mineral Research*, 431-438.

Lanza, R. (2000). *Handbook of Stem Cells*. Burlington: Academic Press.

Nicholls, D. G., & Ferguson, S. J. (2002). *Bioenergetics*. Academic Press.

Nucleus pulposus. (2008, Oct. 17). Retrieved Sep. 2, 2010, from Wikipedia: en.wikipedia.org/wiki/Nucleus_pulposus Ramsey, K. M., Marcheva, B., Kohsaka, A., & Bass, J. (2007). The Clockwork of Metabolism. *Annu. Rev. Nutr.*, 219-240.

Trock, D. H. (2000). Electromagnetic Fields and Magnets: Investigational Treatment of Musculoskeletal Disorders. *Rheumatic Disease Clinics of North America*, 51-62.

What is claimed is:

1. A method to modulate an increase, decrease, or both increase and decrease in the expression level of at least one gene or gene family comprising the steps of:
   tuning at least one predetermined profile of at least one time-varying stimulation field thereby resulting in at least one tuned time-varying stimulation field comprised of at least one tuned predetermined profile, wherein said step of tuning is comprised of,
      providing at least one set of cellular samples in at least one rotating wall vessel;
      exposing said at least one set of cellular samples to at least one experimental time-varying stimulation field comprising at least one experimental predetermined profile;
      conducting at least one gene expression analyses of said at least one set of cellular samples;
      examining and determining an anabolic effect, catabolic effect, or no effect from the results of said at least one gene expression analyses;
      generating at least one conclusion from said step of examining and determining;
      comparing said at least one conclusion with predetermined criteria;
      if said at least one conclusion does not meet said predetermined criteria, adjusting said at least one experimental predetermined profile based on said at least one conclusion and repeating said steps of providing, exposing, conducting, examining and determining, generating, and comparing; and
      if said at least one conclusion does meet said predetermined criteria, selecting said at least one tuned time-varying stimulation field comprised of said at least one tuned predetermined profile for a predetermined tuned exposure time or a plurality of tuned exposure time sequences,
   wherein said at least one tuned predetermined profile is comprised of a plurality of tuned predetermined figures of merit and is controllable through manipulation of at least one of said plurality of tuned predetermined figures of merit, wherein said plurality of tuned predetermined figures of merit is comprised of two or more of the following: a tuned B-Field magnitude, tuned rising slew rate, tuned rise time, tuned falling slew rate, tuned fall time, tuned frequency, tuned wavelength, and tuned duty cycle;
      controlling said at least one tuned predetermined profile comprised of manipulating said tuned B-Field magnitude to a first value between about 0.6 G to about 200 G and said tuned falling slew rate to a second value between about 2.0 kG/s and about 500.0 kG/s thereby resulting in a controlled at least one tuned time-varying stimulation field comprised of a controlled at least one tuned predetermined profile; and
   exposing mammalian chondrocytes, osteoblasts, osteocytes, osteoclasts, nucleus pulposus, associated tissue, or any combination thereof to said controlled at least one tuned time-varying stimulation field comprised of said controlled at least one tuned predetermined profile for said predetermined tuned exposure time or said plurality of tuned exposure time sequences thereby resulting in said increase, decrease, or both increase and decrease in the expression level of at least one gene or gene family selected from the group consisting of Wnt signaling family, WSP family, forkhead box (FOX) family, sex determining region Y (SRY) SOX family, parathyroid hormone (PTH) family, transforming growth factor (TGF) beta (TGF-β) super family, latent TGF family (ECM), integrin family (Cell Sulfur-Based (SUR): ECM), interleukin (IL) family (cellular cytokine response), thrombospodin family (COMPs), laminin family, proteoglycan family, osteoglycin, collagen family, insulin family, a disintegrin and metalloproteinase (ADAM) family, ADAM with thrombospondin motifs (ADAMTS) family, matrix metallopeptidase (MMP) family, actin family, catenin family, cadherin super family, B-cell lymphoma (BCL) family, calmodulin calcium-modulated gene, calumenin, cathepsin family, clusterin, cytochrome P 450 super family, endoglin, fibrillin family, fibroblast growth factor (FGF) family, leptin, MAP kinase activated protein kinases (MAPKAP) family, MSX homeobox family, NOTCH family, myotilin-myopalladin-palladin family, peroxisome proliferator-activated receptors (PPARA), Platelet Derived Growth Factor (PDGF) family, reticulocalbin, RUNX runt related transcription factors, signal transducer and activator of transcription (STAT) family, SMAD family, stanniocalcin family, SOD super oxide dismutase family, syndecan family, tumor necrosis factor (TNF) super family, AKT/PKB signaling family, and importin family.

2. The method of claim 1, wherein said step of controlling is further comprised of manipulating at least one of the following said plurality of tuned predetermined figures of merit: said tuned rising slew rate, said tuned rise time, said tuned fall time, said tuned frequency, said tuned wavelength, and said tuned duty cycle.

3. The method of claim 1, wherein said at least one set of cellular samples is selected from the group consisting of human chondrocytes, nucleus pulposus, osteoblasts, osteoclasts, and osteocytes as well as associated tissue.

4. The method of claim 1, wherein said step of examining and determining is comprised of:
   selecting at least one gene or gene family selected from the group consisting of Wnt signaling family, WSP family, forkhead box (FOX) family, sex determining region Y (SRY) SOX family, parathyroid hormone (PTH) family, transforming growth factor (TGF) beta (TGF-β) super family, latent TGF family (ECM), integrin family (Cell Sulfur-Based (SUR): ECM), interleukin (IL) family (cellular cytokine response), thrombospodin family (COMPs), laminin family, proteoglycan family, osteoglycin, collagen family, insulin family, a disintegrin and metalloproteinase (ADAM) family, ADAM with thrombospondin motifs (ADAMTS) family, matrix metallopeptidase (MMP) family, actin family, catenin family, cadherin super family, B-cell lymphoma (BCL) family, calmodulin calcium-modulated gene, calumenin, cathepsin family, clusterin, cytochrome P 450 super family, endoglin, fibrillin family, fibroblast growth factor (FGF) family, leptin, MAP kinase activated protein kinases (MAPKAP) family, MSX homeobox family, NOTCH family, myotilin-myopalladin-palladin family, peroxisome proliferator-activated receptors (PPARA), Platelet Derived Growth Factor (PDGF) family, reticulocalbin, RUNX runt related transcription factors, signal transducer and activator of transcription (STAT) family, SMAD family, stanniocalcin family, SOD super oxide dismutase family, syndecan family, tumor necrosis factor (TNF) super family, AKT/PKB signaling family, and importin family;

calculating a fold change for each gene in said selected at least one gene or gene family from the results of said at least one gene expression analyses; and classifying each of said fold change as said anabolic effect, catabolic effect, or no effect.

5. The method of claim 4, wherein said step of generating is comprised of:

establishing a relative value for each of said anabolic effect or catabolic effect;

comparing each of said relative value in combination; and selecting at least one conclusion comprised of either a substantive net anabolic effect, a substantive net catabolic effect, or no determinative effect.

6. The method of claim 1, wherein said step of exposing is comprised of:

providing a stimulation field generator apparatus capable of generating said controlled at least one tuned time-varying stimulation field and located in proximate spatial relationship to said mammalian chondrocytes, osteoblasts, osteocytes, osteoclasts, nucleus pulposus, associated tissue, or any combination thereof; and generating said controlled at least one tuned time-varying stimulation field through operation of said stimulation field generator apparatus.

7. The method of claim 6, wherein said stimulation field generator apparatus is comprised of:

a power source;

a control component operably connected to said power source; and a transmission component operably connected to said control component and said power source, wherein in said step of providing a stimulation field generator apparatus in proximate spatial relationship to said mammalian chondrocytes, osteoblasts, osteocytes, osteoclasts, nucleus pulposus, associated tissue, or any combination thereof, said transmission component is in proximate spatial relationship to said mammalian chondrocytes, osteoblasts, osteocytes, osteoclasts, nucleus pulposus, associated tissue, or any combination thereof.

8. The method of claim 1, wherein said first value is between about 0.6 G to about 50 G and wherein said step of controlling is further comprised of manipulating said rising slew rate having a third value between about 2.0 kG/s and about 50.0 kG/s.

9. The method of claim 1, wherein said first value is between about 0.6 G to about 50 G and wherein said step of controlling is further comprised of manipulating said rising slew rate having a third value between about 2.5 kG/s and about 15.5 kG/s.

10. The method of claim 9, wherein said first value is about 0.65 G and said at least one tuned predetermined profile is comprised of substantially a square wave.

11. The method of claim 1, wherein said first value is between about 0.6 G to about 100 G.

12. The method of claim 11, wherein second value is between about 2.5 kG/s and about 15.5 kG/s.

13. The method of claim 1, wherein said first value is between about 0.6 G to about 100 G and wherein said step of controlling is further comprised of manipulating said tuned duty cycle having a fourth value between about 65% to about 80%.

14. The method of claim 1, wherein said step of controlling is further comprised of manipulating said tuned frequency having a fifth value between about 9 Hz to about 200 Hz.

15. The method of claim 14, wherein said fifth value is between about 10 Hz to about 16 Hz.

16. The method of claim 1, wherein said predetermined tuned exposure time is from about 1 hour to about 1200 hours.

17. The method of claim 1, wherein said first value is about 0.65 G, and said second value is between about 4.5 kG/s to about 15.5 kG/s, and wherein said step of controlling is further comprised of manipulating:

said tuned frequency having a fifth value between about 10 Hz to about 16 Hz, said tuned wavelength having a sixth value between about 250 ms to about 600 ms, and said tuned duty cycle having a fourth value between about 65% to about 80%.

18. A method to modulate an increase, decrease, or both increase and decrease in the expression level of at least one gene or gene family comprising the steps of:

tuning at least one predetermined profile of at least one time-varying stimulation field thereby resulting in at least one tuned time-varying stimulation field comprised of at least one tuned predetermined profile, wherein said at least one tuned predetermined profile is comprised of a plurality of tuned predetermined figures of merit and is controllable through manipulation of at least one of said plurality of tuned predetermined figures of merit, wherein said plurality of tuned predetermined figures of merit is comprised of two or more of the following: a tuned B-Field magnitude, tuned rising slew rate, tuned rise time, tuned falling slew rate, tuned fall time, tuned frequency, tuned wavelength, and tuned duty cycle;

controlling said at least one tuned predetermined profile comprised of manipulating, said tuned B-Field magnitude having a first value of about 0.65 G, said tuned falling slew rate having a second value between about 4.5 kG/s to about 15.5 kG/s, said tuned rising slew rate having a third value between about 2.0 kG/s and to about 4.5 kG/s, said tuned frequency having a fifth value between about 10 Hz to about 200 Hz, said tuned wavelength having a sixth value of about 500 ms, said tuned duty cycle having a fourth value between about 65% to about 80%, thereby resulting in a controlled at least one tuned time-varying stimulation field comprised of a controlled at least one tuned predetermined profile; and exposing mammalian chondrocytes, osteoblasts, osteocytes, osteoclasts, nucleus pulposus, associated tissue, or any combination thereof to said controlled at least one tuned time-varying stimulation field comprised of said controlled at least one tuned predetermined profile for a tuned exposure time of about 720 hours thereby resulting in said increase, decrease, or both increase and decrease in the expression level of at least one gene or gene family selected from the group consisting of Wnt signaling family, WSP family, forkhead box (FOX) family, sex determining region Y (SRY) SOX family, parathyroid hormone (PTH) family, transforming growth factor (TGF) beta (TGF-β) super family, latent TGF family (ECM), integrin family (Cell Sulfur-Based (SUR): ECM), interleukin (IL) family (cellular cytokine response), thrombospodin family (COMPs), laminin family, proteoglycan family, osteoglycin, collagen family, insulin family, a disintegrin and metalloproteinase (ADAM) family, ADAM with thrombospondin motifs (ADAMTS) family, matrix metallopeptidase (MMP) family, actin family, catenin family, cadherin super family, B-cell lymphoma (BCL) family, calmodulin calcium-modulated gene, calumenin, cathepsin family, clusterin, cytochrome P 450 super family, endoglin, fibrillin family, fibroblast growth factor (FGF) family, leptin, MAP kinase activated protein kinases (MAP-KAP) family, MSX homeobox family, NOTCH family, myotilin-myopalladin-palladin family, peroxisome proliferator-activated receptors (PPARA), Platelet Derived Growth Factor (PDGF) family, reticulocalbin, RUNX runt related transcription factors, signal transducer and activator of transcription (STAT) family, SMAD family, stanniocalcin family, SOD super oxide dismutase family, syndecan family, tumor necrosis factor (TNF) super family, AKT/PKB signaling family, and importin family.

19. A method to modulate an increase, decrease, or both increase and decrease in the expression level of at least one gene or gene family comprising the steps of:
tuning at least one predetermined profile of at least one time-varying stimulation field thereby resulting in at least one tuned time-varying stimulation field comprised of at least one tuned predetermined profile, wherein said at least one tuned predetermined profile is comprised of a plurality of tuned predetermined figures of merit and is controllable through manipulation of at least one of said plurality of tuned predetermined figures of merit, wherein said plurality of tuned predetermined figures of merit is comprised of two or more of the following: a tuned B-Field magnitude, tuned rising slew rate, tuned rise time, tuned falling slew rate, tuned fall time, tuned frequency, tuned wavelength, and tuned duty cycle;
controlling said at least one tuned predetermined profile comprised of manipulating said tuned B-Field magnitude to a first value between about 0.6 G to about 200 G and said tuned falling slew rate to a second value between about 2.0 kG/s and about 500.0 kG/s thereby resulting in a controlled at least one tuned time-varying stimulation field comprised of a controlled at least one tuned predetermined profile;
exposing mammalian chondrocytes, osteoblasts, osteocytes, osteoclasts, nucleus pulposus, associated tissue, or any combination thereof to said controlled at least one tuned time-varying stimulation field comprised of said controlled at least one tuned predetermined profile for a predetermined tuned exposure time or plurality of tuned exposure time sequences thereby resulting in said increase, decrease, or both increase and decrease in the expression level of at least one gene or gene family selected from the group consisting of Wnt signaling family, WSP family, forkhead box (FOX) family, sex determining region Y (SRY) SOX family, parathyroid hormone (PTH) family, transforming growth factor (TGF) beta (TGF-β) super family, latent TGF family (ECM), integrin family (Cell Sulfur-Based (SUR): ECM), interleukin (IL) family (cellular cytokine response), thrombospodin family (COMPs), laminin family, proteoglycan family, osteoglycin, collagen family, insulin family, a disintegrin and metalloproteinase (ADAM) family, ADAM with thrombospondin motifs (ADAMTS) family, matrix metallopeptidase (MMP) family, actin family, catenin family, cadherin super family, B-cell lymphoma (BCL) family, calmodulin calcium-modulated gene, calumenin, cathepsin family, clusterin, cytochrome P 450 super family, endoglin, fibrillin family, fibroblast growth factor (FGF) family, leptin, MAP kinase activated protein kinases (MAP-KAP) family, MSX homeobox family, NOTCH family, myotilin-myopalladin-palladin family, peroxisome proliferator-activated receptors (PPARA), Platelet Derived Growth Factor (PDGF) family, reticulocalbin, RUNX runt related transcription factors, signal transducer and activator of transcription (STAT) family, SMAD family, stanniocalcin family, SOD super oxide dismutase family, syndecan family, tumor necrosis factor (TNF) super family, AKTIPKB signaling family, and importin family, wherein said mammalian chondrocytes, osteoblasts, osteocytes, osteoclasts, nucleus pulposus, associated tissue, or any combination thereof are localized in a predetermined region of interest; and introducing Vitamin D, Vitamin K, or both to said region of interest.

20. The method of claim 1, further comprising the step of adding a predetermined amplification factor of predetermined value to said tuned B-Field magnitude.

* * * * *